US008715653B2

(12) United States Patent
Turley et al.

(10) Patent No.: US 8,715,653 B2
(45) Date of Patent: May 6, 2014

(54) MODULATION OF RHAMM (CD168) FOR SELECTIVE ADIPOSE TISSUE DEVELOPMENT

(75) Inventors: Eva A. Turley, London (CA); Mina J. Bissell, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 117 days.

(21) Appl. No.: 12/515,405

(22) PCT Filed: Nov. 21, 2007

(86) PCT No.: PCT/US2007/085453
§ 371 (c)(1),
(2), (4) Date: Feb. 9, 2010

(87) PCT Pub. No.: WO2008/140586
PCT Pub. Date: Nov. 20, 2008

(65) Prior Publication Data
US 2010/0143382 A1 Jun. 10, 2010

Related U.S. Application Data

(60) Provisional application No. 60/860,606, filed on Nov. 21, 2006, provisional application No. 60/860,607, filed on Nov. 21, 2006.

(51) Int. Cl.
*A61K 39/395* (2006.01)
*A61K 39/00* (2006.01)

(52) U.S. Cl.
USPC .................. 424/130.1; 424/139.1; 424/184.1

(58) Field of Classification Search
None
See application file for complete search history.

(56) References Cited

U.S. PATENT DOCUMENTS

| | | | |
|---|---|---|---|
| 8,093,217 B2 * | 1/2012 | Toole et al. ................. | 514/19.3 |
| 2002/0127227 A1 | 9/2002 | Holmes et al. | |
| 2003/0100490 A1 * | 5/2003 | Cruz et al. ................. | 514/12 |
| 2003/0170755 A1 | 9/2003 | Schmitt et al. | |
| 2004/0037834 A1 | 2/2004 | Woloski et al. | |
| 2005/0058646 A1 | 3/2005 | Turley et al. | |
| 2007/0179085 A1 | 8/2007 | Savani | |
| 2010/0062000 A1 | 3/2010 | Turley et al. | |

FOREIGN PATENT DOCUMENTS

| | | |
|---|---|---|
| EP | 0950708 A2 | 10/1999 |
| WO | WO/2008/140586 | 11/2008 |

OTHER PUBLICATIONS

Feldman et al (Transplant. Proc. 1998, 30, 4126-4127.*
Mestas et al . J. of Immunology, 2004, 172, pp. 2731-238).*
Tufveson et al., ( Immun. Review 1993, N136, pp. 101-107.*
Greiner et al ( Blood, 2005,v.106, Abstract 2781).*
International Search Report and Written Opinion dated Nov. 7, 2008 issued in WO/2008/ 140586 (PCT/US2007/085453).
International Preliminary Report on Patentibility dated May 26, 2009 issued in WO/2008/140586 (PCT/US2007/085453).
European Supplemental Search report dated Mar. 4, 2010 issued in EP07874313.5.
European Examination Report dated Jun. 21, 2010 issued in EP07874313.5.
Adamia et al. (2005) "Hyaluronan and hyaluronan synthases: potential therapeutic targets in cancer.", *Curr Drug Targets Cardiovasc Haematol Disord* 5: 3-14.
Aitken et al., (2001) "Stretch-Induced Bladder Smooth Muscle Cell (SMC) Proliferation Is Mediated by RHAMM Dependent Extracellular-Regulated Kinase (erk) Signaling.", *Urology* 57(Supp 6A):109.
Bissell (2001) "Chronic liver injury, TGF-beta, and cancer.", *Exp Mol Med* 33:179-190.
Cheon et al. (2002) "beta-Catenin stabilization dysregulates mesenchymal cell proliferation, motility, and invasiveness and causes aggressive fibromatosis and hyperplastic cutaneous wounds.", *Proc. Natl. Acad. Sci.* 99(10): 6973-6978.
Cheung et al. (1999) "Receptor for hyaluronan mediated motility (RHAMM), a hyaladherin that regulates cell responses to growth factors.", *Biochem Soc Trans* 27: 135-142.
Domaszewska et al. (2006) "Dermal keratinocytes—protective mechanical, biochemical and immune functions related to grafting.", *Ann. Transplnt.* 11(4): 45-52.
Fu et al. (2006) "Enhanced wound-healing quality with bone marrow mesenchymal stem cells autografting after skin injury.", *Wound Repair Regen.* 14: 325-335.
Fukumura et al. (2003) "Paracrine regulation of angiogenesis and adipocyte differentiation during vivo adipogenesis.", *Circulation Research* 93(9): E88-E97.
Hall et al. (1995) "Overexpression of the hyaluronan receptor RHAMM is transforming and is also required for H-ras transformation.", *Cell* 82: 19-28.
Hall et al. (1996) "pp60(c-src) is required for cell locomotion regulated by the hyaluronanreceptor RHAMM.", *Oncogene* 13: 2213-2224.
Hall et al. (2001) "Fibroblasts require protein kinase C activation to respond to hyaluronan with increased locomotion.", *Matrix Biol* 20: 183-192.
Hardwick et al. (1992) "Molecular cloning of a novel hyaluronan receptor that mediates tumor cell motility.", *J Cell Biol.*, 117(6):1343-1350.
Huang et al. (2004) "MAP kinases and cell migration.", *J Cell Sci* 117: 4619-4628.
Kaya et al. (1997) "Selective suppression of CD44 in keratinocytes of mice bearing an antisense CD44 transgene driven by a tissue-specific promoter disrupts hyaluronate metabolism in the skin and impairs keratinocyte proliferation.", *Genes and Development* 11(8):996-1007.
Li et al. (2006) "Adult bone-marrow-derived mesenchymal stem cells contribute to wound healing of skin appendages.", *Cell Tissue Res*, 326(3): 725-736.

(Continued)

*Primary Examiner* — Michail Belyavskyi
(74) *Attorney, Agent, or Firm* — Tom Hunter; Weaver Austin Villeneuve & Sampson LLP

(57) ABSTRACT

Herein is described the methods and compositions for modulation of Rhamm, also known as CD 186, and its effects on wound repair, muscle differentiation, bone density and adipogeneisis through its ability to regulate mesenchymal stem cell differentiation. Compositions and methods are provided for blocking Rhamm function for selectively increasing subcutaneous, but not, visceral fat. Compositions and methods for modulating Rhamm in wound repair are also described.

19 Claims, 17 Drawing Sheets

(56) References Cited

OTHER PUBLICATIONS

Lovvorn et al. (1998) "Hyaluronan receptor expression increases in fetal excisional skin wounds and correlates with fibroplasia.", *J Pediatr Surg* 33: 1062-1069.

Mansilla et al. (2006) "Bloodstream cells phenotypically identifical to human mesenchymal bone marrow stem cells circulate in large amounts under the influence of acute large skin damage: new evidence for their use in regenerative medicine.", *Transplant Proc.* 38: 967-969.

Nedvetzki et al. (2004) "RHAMM, a receptor for hyaluronan-mediated motility, compensates for CD44 in inflamed CD44-knockout mice: A different interpretation of redundancy.", *Proc. Natl. Acad. Sci. USA*, 101:18081-18086.

Nickel (2005) "Unconventional secretory routes: direct protein export across the plasma membrane of mammalian cells.", *Traffic* 6:607-614.

Park et al. (2000) "The influence of the microenvironment on the malignant phenotype.", *Mol Med Today* 6: 324-329.

Providence and Higgins (2004) "PAI-1 expression is required for epithelial cell migration in two distinct phases of in vitro wound repair.", *J Cell Physiol* 200: 297-308.

Reid et al. (2004) "The future of wound healing: pursuing surgical models in transgenic and knockout mice.", *J Am Coll Surg* 199: 578-585.

Samuel et al. (1993) "TGF-beta 1 stimulation of cell locomotion utilizes the hyaluronan receptor RHAMM and hyaluronan.",*J. Cell Biol* 123: 749-758.

Savani et al. (1995) "Migration of bovine aortic smooth muscle cells after wounding injury. The role of hyaluronan and RHAMM.", *J Clin Invest* 95: 1158-1168.

Schmits et al. (1997) "CD44 regulates hematopoietic progenitor distribution, granuloma formation, and tumorigenicity.", *Blood* 90: 2217-2233.

Shumakov (2003) "Mesenchymal bone marrow stem cells more effectively stimulate regeneration of deep burn wounds than embryonic fibroblasts.", *Bull Exp Biol Med* 136: 192-195.

Tammi et al. (2002) "Hyaluronan and homeostasis: a balancing act.", *J Biol Chem* 277: 4581-4584.

Tolg et al. (2003) "Genetic deletion of receptor for hyaluronan-mediated motility (Rhamm) attenuates the formation of aggressive fibromatosis (desmoid tumor).", *Oncogene* 22:6873-6882.

Tolg et al. (2006) "Rhamm -/- fiibroblasts are defective in CD44-mediated ERK1, 2 motogenic signaling, leading to defective skin wound repair", *J Cell Biol* 175(6):1017-1028.

Toole (2004) "Hyaluronan: from extracellular glue to pericellular cue.", *Nat Rev Cancer* 4:528-539.

Turley (1982) "Purification of a hyaluronate-binding protein fraction that modifies cell social behavior.", *Biochem Biophys Res Commun* 108: 1016-1024.

Turley et al. (2002) "Signaling properties of hyaluronan receptors.", *J Biol Chem* 277(7): 4589-4592.

Zhang et al. (1998) "The hyaluronan receptor RHAMM regulates extracellular-regulated kinase.", *J Biol Chem* 273:11342-11348.

European Examination Report dated Nov. 15, 2011 issued in EP07874313.5.

Australian Examination Report dated Apr. 23, 2012 issued in AU2007353332.

European Partial Search report dated Feb. 11, 2013 issued in EP12172124.5.

European Extended Search report dated Jun. 5, 2013 issued in EP12172124.5.

\* cited by examiner

A. Tenascin protein expression in wound sections

B. Areas of tenascin-positive granulation tissue

A. Random motility in response to HA

B. CD44 protein expression b. Invasion into collagen gels a. Migration into scratch wounds

SEQUENCE LISTING

<160> NUMBER OF SEQ ID NOS: 11

<210> SEQ ID NO 1
<211> LENGTH: 2957
<212> TYPE: DNA
<213> ORGANISM: Homo sapiens

```
<400> SEQUENCE: 1
gccagtcacc ttcagtttct ggagctggcc gtcaacatgt cctttcctaa ggcgcccttg      60
aaacgattca atgacccttc tggttgtgca ccatctccag gtgcttatga tgttaaaact     120
ttagaagtat tgaaaggacc agtatccttt cagaaatcac aaagatttaa acaacaaaaa     180
gaatctaaac aaaatcttaa tgttgacaaa gatactacct tgcctgcttc agctagaaaa     240
gttaagtctt cggaatcaaa gattcgtgtt cttctacagg aacgtggtgc ccaggacagc     300
cggatccagg atctggaaac tgagttggaa aagatggaag caaggctaaa tgctgcacta     360
agggaaaaaa catctctctc tgcaataat gctacactgg aaaaacaact tattgaattg     420
accaggacta atgaactact aaaatctaag ttttctgaaa atggtaacca gaagaatttg     480
agaattctaa gcttggagtt gatgaaactt agaaacaaaa gagaaacaaa gatgaggggt     540
atgatggcta agcaagaagg catggagatg aagctgcagg tcacccaaag gagtctcgaa     600
gagtctcaag ggaaaatagc ccaactggag ggaaaacttg tttcaataga gaagaaaag     660 attgatgaaa atctgaaac agaaaaactc ttggaataca tcgaagaaat tagttgtgct     720
tcagatcaag tggaaaaata caagctagat attgcccagt tagaagaaaa tttgaaagag     780
aagaatgatg aaattttaag ccttaagcag tctcttgagg agaatattgt tatattatct     840
aaacaagtag aagatctaaa tgtgaaatgt cagctgcttg aaaaagaaaa agaagaccat     900
gtcaacagga atagagaaca caacgaaaat ctaaatgcag agatgcaaaa cttaaaacag     960
aagtttattc ttgaacaaca ggaacgtgaa aagcttcaac aaaaagaatt acaaattgat    1020
tcacttctgc aacaagagaa agaattatct tcgagtcttc atcagaagct ctgttctttt    1080
caagaggaaa tggttaaaga gaagaatctg tttgaggaag aattaaagca aacactggat    1140
gagcttgata attacagca aaaggaggaa caagctgaaa ggctggtcaa gcaattggaa    1200
gaggaagcaa aatctagagc tgaagaatta aaactcctag aagaaaagct gaaagggaag    1260
gaggctgaac tggagaaaag tagtgctgct cataccccagg ccaccctgct tttgcaggaa    1320
aagtatgaca gtatggtgca aagccttgaa gatgttactg ctcaatttga aagctataaa    1380
gcgttaacag ccagtgagat agaagatctt aagctggaga actcatcatt acaggaaaaa    1440
gcggccaagg ctgggaaaaa tgcagaggat gttcagcatc agattttggc aactgagagc    1500
tcaaatcaag aatatgtaag gatgcttcta gatctgcaga ccaagtcagc actaaaggaa    1560
acagaaatta agaaatcac agtttctttt cttcaaaaaa taactgattt gcagaaccaa    1620
ctcaagcaac aggaggaaga ctttagaaaa cagctggaag atgaagaagg aagaaaagct    1680
gaaaaagaaa atacaacagc agaattaact gaagaaatta caagtggcg tctcctctat    1740 gaagaactat ataataaaac aaaaccttt cagctacaac tagatgcttt tgaagtagaa    1800
aaacaggcat tgttaatga acatggtgca gctcaggaac agctaaataa aataagagat    1860
tcatatgcta aattattggg tcatcagaat ttgaaacaaa aatcaagca tgttgtgaag    1920 ttgaaagatg aaaatagcca actcaaatcg gaagtatcaa aactccgctg tcagcttgct    1980
aaaaaaaaac aaagtgagac aaaacttcaa gaggaattga ataaagttct aggtatcaaa    2040
cactttgatc cttcaaaggc ttttcatcat gaaagtaaag aaaattttgc cctgaagacc    2100
ccattaaaag aaggcaatac aaactgttac cgagctccta tggagtgtca agaatcatgg    2160
aagtaaacat ctgagaaacc tgttgaagat tatttcattc gtcttgttgt tattgatgtt    2220
gctgttatta tatttgacat gggtatttta taatgttgta tttaatttta actgccaatc    2280
cttaaatatg tgaaaggaac attttttacc aaagtgtctt ttgacatttt attttttctt    2340
```

-continued

```
gcaaatacct cctccctaat gctcacctttt atcacctcat tctgaaccct ttcgctggct    2400
ttccagctta gaatgcatct catcaactta aaagtcagta tcatattatt atcctcctgt    2460
tctgaaacct tagtttcaag agtctaaacc ccagattctt cagcttgatc ctggaggtct    2520
tttctagtct gagcttcttt agctaggcta aaacaccttg gcttgttatt gcctctactt    2580
tgattctgat aatgctcact tggtcctacc tattatcctt ctacttgtcc agttcaaata    2640
agaaataagg acaagcctaa cttcatagaa acctctctat ttttaatcag ttgtttaata    2700
atttacaggt tcttaggctc catcctgttt gtatgaaatt ataatctgtg gattggcctt    2760
taagcctgca ttcttaacaa actcttcagt taattcttag atacactaaa aatctgagaa    2820
actctacatg taactatttc ttcagagttt gtcatatact gcttgtcatc tgcatgtcta    2880
ctcagcattt gattaacatt tgtgtaatat gaaataaaat tacacagtaa gtcatttaac    2940
caaaaaaaaa aaaaaaa                                                   2957
```

<210> SEQ ID NO 2
<211> LENGTH: 709
<212> TYPE: PRT
<213> ORGANISM: Homo sapiens

<400> SEQUENCE: 2

```
Met Ser Phe Pro Lys Ala Pro Leu Lys Arg Phe Asn Asp Pro Ser Gly
1               5                   10                  15

Cys Ala Pro Ser Pro Gly Ala Tyr Asp Val Lys Thr Leu Glu Val Leu
            20                  25                  30

Lys Gly Pro Val Ser Phe Gln Lys Ser Gln Arg Phe Lys Gln Gln Lys
        35                  40                  45

Glu Ser Lys Gln Asn Leu Asn Val Asp Lys Asp Thr Thr Leu Pro Ala
    50                  55                  60

Ser Ala Arg Lys Val Lys Ser Glu Ser Lys Ile Arg Val Leu Leu
65                  70                  75                  80

Gln Glu Arg Gly Ala Gln Asp Ser Arg Ile Gln Asp Leu Glu Thr Glu
                85                  90                  95

Leu Glu Lys Met Glu Ala Arg Leu Asn Ala Ala Leu Arg Glu Lys Thr
            100                 105                 110

Ser Leu Ser Ala Asn Asn Ala Thr Leu Glu Lys Gln Leu Ile Glu Leu
        115                 120                 125

Thr Arg Thr Asn Glu Leu Leu Lys Ser Lys Phe Ser Glu Asn Gly Asn
    130                 135                 140

Gln Lys Asn Leu Arg Ile Leu Ser Leu Glu Leu Met Lys Leu Arg Asn
145                 150                 155                 160

Lys Arg Glu Thr Lys Met Arg Gly Met Met Ala Lys Gln Glu Gly Met
                165                 170                 175

Glu Met Lys Leu Gln Val Thr Gln Arg Ser Leu Glu Glu Ser Gln Gly
            180                 185                 190

Lys Ile Ala Gln Leu Glu Gly Lys Leu Val Ser Ile Glu Lys Glu Lys
        195                 200                 205

Ile Asp Glu Lys Ser Glu Thr Glu Lys Leu Leu Glu Tyr Ile Glu Glu
    210                 215                 220

Ile Ser Cys Ala Ser Asp Gln Val Glu Lys Tyr Lys Leu Asp Ile Ala
225                 230                 235                 240

Gln Leu Glu Glu Asn Leu Lys Glu Lys Asn Asp Glu Ile Leu Ser Leu
                245                 250                 255

Lys Gln Ser Leu Glu Glu Asn Ile Val Ile Leu Ser Lys Gln Val Glu
```

-continued

```
            260                 265                 270
Asp Leu Asn Val Lys Cys Gln Leu Leu Glu Lys Glu Lys Glu Asp His
        275                 280                 285
Val Asn Arg Asn Arg Glu His Asn Glu Asn Leu Asn Ala Glu Met Gln
    290                 295                 300
Asn Leu Lys Gln Lys Phe Ile Leu Glu Gln Gln Glu Arg Glu Lys Leu
305                 310                 315                 320
Gln Gln Lys Glu Leu Gln Ile Asp Ser Leu Leu Gln Gln Glu Lys Glu
                325                 330                 335
Leu Ser Ser Ser Leu His Gln Lys Leu Cys Ser Phe Gln Glu Glu Met
                340                 345                 350
Val Lys Glu Lys Asn Leu Phe Glu Glu Glu Leu Lys Gln Thr Leu Asp
        355                 360                 365
Glu Leu Asp Lys Leu Gln Gln Lys Glu Glu Gln Ala Glu Arg Leu Val
    370                 375                 380
Lys Gln Leu Glu Glu Glu Ala Lys Ser Arg Ala Glu Glu Leu Lys Leu
385                 390                 395                 400
Leu Glu Glu Lys Leu Lys Gly Lys Glu Ala Glu Leu Glu Lys Ser Ser
                405                 410                 415
Ala Ala His Thr Gln Ala Thr Leu Leu Leu Gln Glu Lys Tyr Asp Ser
                420                 425                 430
Met Val Gln Ser Leu Glu Asp Val Thr Ala Gln Phe Glu Ser Tyr Lys
        435                 440                 445
Ala Leu Thr Ala Ser Glu Ile Glu Asp Leu Lys Leu Glu Asn Ser Ser
    450                 455                 460
Leu Gln Glu Lys Ala Ala Lys Ala Gly Lys Asn Ala Glu Asp Val Gln
465                 470                 475                 480
His Gln Ile Leu Ala Thr Glu Ser Ser Asn Gln Glu Tyr Val Arg Met
                485                 490                 495
Leu Leu Asp Leu Gln Thr Lys Ser Ala Leu Lys Glu Thr Glu Ile Lys
                500                 505                 510
Glu Ile Thr Val Ser Phe Leu Gln Lys Ile Thr Asp Leu Gln Asn Gln
        515                 520                 525
Leu Lys Gln Gln Glu Glu Asp Phe Arg Lys Gln Leu Glu Asp Glu Glu
    530                 535                 540
Gly Arg Lys Ala Glu Lys Glu Asn Thr Thr Ala Glu Leu Thr Glu Glu
545                 550                 555                 560
Ile Asn Lys Trp Arg Leu Leu Tyr Glu Glu Leu Tyr Asn Lys Thr Lys
                565                 570                 575
Pro Phe Gln Leu Gln Leu Asp Ala Phe Glu Val Glu Lys Gln Ala Leu
                580                 585                 590
Leu Asn Glu His Gly Ala Ala Gln Glu Gln Leu Asn Lys Ile Arg Asp
        595                 600                 605
Ser Tyr Ala Lys Leu Leu Gly His Gln Asn Leu Lys Gln Lys Ile Lys
    610                 615                 620
His Val Val Lys Leu Lys Asp Glu Asn Ser Gln Leu Lys Ser Glu Val
625                 630                 635                 640
Ser Lys Leu Arg Cys Gln Leu Ala Lys Lys Lys Gln Ser Glu Thr Lys
                645                 650                 655
Leu Gln Glu Glu Leu Asn Lys Val Leu Gly Ile Lys His Phe Asp Pro
                660                 665                 670
Ser Lys Ala Phe His His Glu Ser Lys Glu Asn Phe Ala Leu Lys Thr
        675                 680                 685
```

Pro Leu Lys Glu Gly Asn Thr Asn Cys Tyr Arg Ala Pro Met Glu Cys
        690                 695                 700

Gln Glu Ser Trp Lys
705

<210> SEQ ID NO 3
<211> LENGTH: 3002
<212> TYPE: DNA
<213> ORGANISM: Homo sapiens

<400> SEQUENCE: 3

| | | | | | |
|---|---|---|---|---|---|
| gccagtcacc | ttcagtttct | ggagctggcc | gtcaacatgt | cctttcctaa | ggcgcccttg | 60 |
| aaacgattca | atgacccttc | tggttgtgca | ccatctccag | gtgcttatga | tgttaaaact | 120 |
| ttagaagtat | tgaaaggacc | agtatccttt | cagaaatcac | aaagatttaa | acaacaaaaa | 180 |
| gaatctaaac | aaaatcttaa | tgttgacaaa | gatactacct | tgcctgcttc | agctagaaaa | 240 |
| gttaagtctt | cggaatcaaa | ggaatctcaa | agaatgata | aagatttgaa | gatattagag | 300 |
| aaagagattc | gtgttcttct | acaggaacgt | ggtgcccagg | acagccggat | ccaggatctg | 360 |
| gaaactgagt | tggaaaagat | ggaagcaagg | ctaaatgctg | cactaaggga | aaaaacatct | 420 |
| ctctctgcaa | ataatgctac | actggaaaaa | caacttattg | aattgaccag | gactaatgaa | 480 |
| ctactaaaat | ctaagttttc | tgaaaatggt | aaccagaaga | atttgagaat | tctaagcttg | 540 |
| gagttgatga | aacttagaaa | caaaagagaa | acaaagatga | ggggtatgat | ggctaagcaa | 600 |
| gaaggcatgg | agatgaagct | gcaggtcacc | caaaggagtc | tcgaagagtc | tcaagggaaa | 660 |
| atagcccaac | tggagggaaa | acttgtttca | atagagaaag | aaaagattga | tgaaaaatct | 720 |
| gaaacagaaa | aactcttgga | atacatcgaa | gaaattagtt | gtgcttcaga | tcaagtggaa | 780 |
| aaatacaagc | tagatattgc | ccagttagaa | gaaaatttga | agagaagaa | tgatgaaatt | 840 |
| ttaagcctta | agcagtctct | tgaggagaat | attgttatat | atctaaaaca | agtagaagat | 900 |
| ctaaatgtga | aatgtcagct | gcttgaaaaa | gaaaagaag | accatgtcaa | caggaataga | 960 |
| gaacacaacg | aaaatctaaa | tgcagagatg | caaaacttaa | aacagaagtt | tattcttgaa | 1020 |
| caacaggaac | gtgaaaagct | tcaacaaaaa | gaattacaaa | ttgattcact | tctgcaacaa | 1080 |
| gagaaagaat | tatcttcgag | tcttcatcag | aagctctgtt | cttttcaaga | ggaaatggtt | 1140 |
| aaagagaaga | atctgtttga | ggaagaatta | aagcaaacac | tggatgagct | tgataaatta | 1200 |
| cagcaaaagg | aggaacaagc | tgaaaggctg | gtcaagcaat | ggaagagga | agcaaaatct | 1260 |
| agagctgaag | aattaaaaact | cctagaagaa | aagctgaaag | gaaggaggc | tgaactggag | 1320 |
| aaaagtagtg | ctgctcatac | ccaggccacc | ctgctttgc | aggaaaagta | tgacagtatg | 1380 |
| gtgcaaagcc | ttgaagatgt | tactgctcaa | tttgaaagct | ataaagcgtt | aacagccagt | 1440 |
| gagatagaag | atcttaagct | ggagaactca | tcattacagg | aaaaagcggc | caaggctggg | 1500 |
| aaaaatgcag | aggatgttca | gcatcagatt | ttggcaactg | agagctcaaa | tcaagaatat | 1560 |
| gtaaggatgc | ttctagatct | gcagaccaag | tcagcactaa | aggaaacaga | aattaaagaa | 1620 |
| atcacagttt | cttttcttca | aaaaataact | gatttgcaga | accaactcaa | gcaacaggag | 1680 |
| gaagactta | gaaacagct | ggaagatgaa | gaaggaagaa | aagctgaaaa | agaaaataca | 1740 |
| acagcagaat | taactgaaga | aattaacaag | tggcgtctcc | tctatgaaga | actatataat | 1800 |
| aaaacaaaac | cttttcagct | acaactagat | gcttttgaag | tagaaaaaca | ggcattgttg | 1860 |
| aatgaacatg | gtgcagctca | ggaacagcta | aataaaataa | gagattcata | tgctaaatta | 1920 |
| ttgggtcatc | agaatttgaa | acaaaaaatc | aagcatgttg | tgaagttgaa | agatgaaaat | 1980 |

-continued

```
agccaactca aatcggaagt atcaaaactc cgctgtcagc ttgctaaaaa aaaacaaagt    2040
gagacaaaac ttcaagagga attgaataaa gttctaggta tcaaacactt tgatccttca    2100
aaggcttttc atcatgaaag taaagaaaat tttgccctga agaccccatt aaaagaaggc    2160
aatacaaact gttaccgagc tcctatggag tgtcaagaat catggaagta acatctgag     2220 aaacctgttg aagattattt cattcgtctt gttgttattg atgttgctgt tattatattt    2280
gacatgggta ttttataatg ttgtatttaa ttttaactgc caatccttaa atatgtgaaa    2340
ggaacatttt ttaccaaagt gtcttttgac attttatttt ttcttgcaaa tacctcctcc    2400
ctaatgctca cctttatcac ctcattctga accctttcgc tggctttcca gcttagaatg    2460
catctcatca acttaaaagt cagtatcata ttattatcct cctgttctga aaccttagtt    2520
tcaagagtct aaaccccaga ttcttcagct tgatcctgga ggtcttttct agtctgagct    2580
tctttagcta ggctaaaaca ccttggcttg ttattgcctc tactttgatt ctgataatgc    2640
tcacttggtc ctacctatta tccttctact tgtccagttc aaataagaaa taaggacaag    2700
cctaacttca tagaaacctc tctattttta atcagttgtt taataattta caggttctta    2760
ggctccatcc tgtttgtatg aaattataat ctgtggattg gcctttaagc ctgcattctt    2820
aacaaactct tcagttaatt cttagataca ctaaaaatct gagaaactct acatgtaact    2880
atttcttcag agtttgtcat atactgcttg tcatctgcat gtctactcag catttgatta    2940
acatttgtgt aatatgaaat aaaattacac agtaagtcat ttaaccaaaa aaaaaaaaaa    3000
aa                                                                   3002
```

<210> SEQ ID NO 4
<211> LENGTH: 724
<212> TYPE: PRT
<213> ORGANISM: Homo sapiens

<400> SEQUENCE: 4

```
Met Ser Phe Pro Lys Ala Pro Leu Lys Arg Phe Asn Asp Pro Ser Gly
 1               5                  10                  15

Cys Ala Pro Ser Pro Gly Ala Tyr Asp Val Lys Thr Leu Glu Val Leu
            20                  25                  30

Lys Gly Pro Val Ser Phe Gln Lys Ser Gln Arg Phe Lys Gln Gln Lys
        35                  40                  45

Glu Ser Lys Gln Asn Leu Asn Val Asp Lys Asp Thr Thr Leu Pro Ala
    50                  55                  60

Ser Ala Arg Lys Val Lys Ser Ser Glu Ser Lys Glu Ser Gln Lys Asn
65                  70                  75                  80

Asp Lys Asp Leu Lys Ile Leu Glu Lys Glu Ile Arg Val Leu Leu Gln
                85                  90                  95

Glu Arg Gly Ala Gln Asp Ser Arg Ile Gln Asp Leu Glu Thr Glu Leu
            100                 105                 110

Glu Lys Met Glu Ala Arg Leu Asn Ala Ala Leu Arg Glu Lys Thr Ser
        115                 120                 125

Leu Ser Ala Asn Asn Ala Thr Leu Glu Lys Gln Leu Ile Glu Leu Thr
    130                 135                 140

Arg Thr Asn Glu Leu Leu Lys Ser Lys Phe Ser Glu Asn Gly Asn Gln
145                 150                 155                 160

Lys Asn Leu Arg Ile Leu Ser Leu Glu Leu Met Lys Leu Arg Asn Lys
                165                 170                 175

Arg Glu Thr Lys Met Arg Gly Met Met Ala Lys Gln Glu Gly Met Glu
            180                 185                 190
```

-continued

```
Met Lys Leu Gln Val Thr Gln Arg Ser Leu Glu Glu Ser Gln Gly Lys
            195                 200                 205
Ile Ala Gln Leu Glu Gly Lys Leu Val Ser Ile Glu Lys Glu Lys Ile
    210                 215                 220
Asp Glu Lys Ser Glu Thr Glu Lys Leu Leu Glu Tyr Ile Glu Glu Ile
225                 230                 235                 240
Ser Cys Ala Ser Asp Gln Val Glu Lys Tyr Lys Leu Asp Ile Ala Gln
                245                 250                 255
Leu Glu Glu Asn Leu Lys Glu Lys Asn Asp Glu Ile Leu Ser Leu Lys
            260                 265                 270
Gln Ser Leu Glu Glu Asn Ile Val Ile Leu Ser Lys Gln Val Glu Asp
    275                 280                 285
Leu Asn Val Lys Cys Gln Leu Leu Glu Lys Lys Glu Asp His Val
290                 295                 300
Asn Arg Asn Arg Glu His Asn Glu Asn Leu Asn Ala Glu Met Gln Asn
305                 310                 315                 320
Leu Lys Gln Lys Phe Ile Leu Glu Gln Gln Glu Arg Glu Lys Leu Gln
                325                 330                 335
Gln Lys Glu Leu Gln Ile Asp Ser Leu Leu Gln Glu Lys Glu Leu
            340                 345                 350
Ser Ser Ser Leu His Gln Lys Leu Cys Ser Phe Gln Glu Glu Met Val
        355                 360                 365
Lys Glu Lys Asn Leu Phe Glu Glu Leu Lys Gln Thr Leu Asp Glu
370                 375                 380
Leu Asp Lys Leu Gln Gln Lys Glu Glu Gln Ala Glu Arg Leu Val Lys
385                 390                 395                 400
Gln Leu Glu Glu Glu Ala Lys Ser Arg Ala Glu Glu Leu Lys Leu Leu
                405                 410                 415
Glu Glu Lys Leu Lys Gly Lys Glu Ala Glu Leu Glu Lys Ser Ser Ala
            420                 425                 430
Ala His Thr Gln Ala Thr Leu Leu Leu Gln Glu Lys Tyr Asp Ser Met
        435                 440                 445
Val Gln Ser Leu Glu Asp Val Thr Ala Gln Phe Glu Ser Tyr Lys Ala
    450                 455                 460
Leu Thr Ala Ser Glu Ile Glu Asp Leu Lys Leu Glu Asn Ser Ser Leu
465                 470                 475                 480
Gln Glu Lys Ala Ala Lys Ala Gly Lys Asn Ala Glu Asp Val Gln His
                485                 490                 495
Gln Ile Leu Ala Thr Glu Ser Ser Asn Gln Glu Tyr Val Arg Met Leu
            500                 505                 510
Leu Asp Leu Gln Thr Lys Ser Ala Leu Lys Glu Thr Glu Ile Lys Glu
        515                 520                 525
Ile Thr Val Ser Phe Leu Gln Lys Ile Thr Asp Leu Gln Asn Gln Leu
    530                 535                 540
Lys Gln Gln Glu Glu Asp Phe Arg Lys Gln Leu Glu Asp Glu Glu Gly
545                 550                 555                 560
Arg Lys Ala Glu Lys Glu Asn Thr Thr Ala Glu Leu Thr Glu Glu Ile
                565                 570                 575
Asn Lys Trp Arg Leu Leu Tyr Glu Glu Leu Tyr Asn Lys Thr Lys Pro
            580                 585                 590
Phe Gln Leu Gln Leu Asp Ala Phe Glu Val Glu Lys Gln Ala Leu Leu
        595                 600                 605
Asn Glu His Gly Ala Ala Gln Glu Gln Leu Asn Lys Ile Arg Asp Ser
    610                 615                 620
```

-continued

```
Tyr Ala Lys Leu Leu Gly His Gln Asn Leu Lys Gln Lys Ile Lys His
625                 630                 635                 640

Val Val Lys Leu Lys Asp Glu Asn Ser Gln Leu Lys Ser Glu Val Ser
                645                 650                 655

Lys Leu Arg Cys Gln Leu Ala Lys Lys Gln Ser Glu Thr Lys Leu
            660                 665                 670

Gln Glu Glu Leu Asn Lys Val Leu Gly Ile Lys His Phe Asp Pro Ser
            675                 680                 685

Lys Ala Phe His His Glu Ser Lys Glu Asn Phe Ala Leu Lys Thr Pro
        690                 695                 700

Leu Lys Glu Gly Asn Thr Asn Cys Tyr Arg Ala Pro Met Glu Cys Gln
705                 710                 715                 720

Glu Ser Trp Lys

<210> SEQ ID NO 5
<211> LENGTH: 14
<212> TYPE: PRT
<213> ORGANISM: Artificial
<220> FEATURE:
<223> OTHER INFORMATION: Hyaluronan binding peptide.

<400> SEQUENCE: 5

Ser Thr Met Met Arg Ser His Lys Thr Arg Ser His His Val
1               5                   10

<210> SEQ ID NO 6
<211> LENGTH: 9
<212> TYPE: PRT
<213> ORGANISM: Homo sapiens

<400> SEQUENCE: 6

Lys Ile Lys His Val Val Lys Leu Lys
1               5

<210> SEQ ID NO 7
<211> LENGTH: 6
<212> TYPE: PRT
<213> ORGANISM: Artificial
<220> FEATURE:
<223> OTHER INFORMATION: Factor Xa cleavage site.
<220> FEATURE:
<221> NAME/KEY: REPEAT
<222> LOCATION: (2)..(2)
<223> OTHER INFORMATION: 1 to n possible repeats

<400> SEQUENCE: 7

Met His Ile Glu Gly Arg
1               5

<210> SEQ ID NO 8
<211> LENGTH: 8
<212> TYPE: PRT
<213> ORGANISM: Artificial
<220> FEATURE:
<223> OTHER INFORMATION: Hyaluronan mimicking peptide.

<400> SEQUENCE: 8

Tyr Asp Ser Glu Tyr Glu Ser Glu
1               5

<210> SEQ ID NO 9
<211> LENGTH: 8
<212> TYPE: PRT
<213> ORGANISM: Artificial
```

```
<220> FEATURE:
<223> OTHER INFORMATION: Hyaluronan mimicking peptide.
<220> FEATURE:
<221> NAME/KEY: VARIANT
<222> LOCATION: (4)..(4)
<223> OTHER INFORMATION: Residue 4 is the D-amino acid isomer
<220> FEATURE:
<221> NAME/KEY: VARIANT
<222> LOCATION: (6)..(6)
<223> OTHER INFORMATION: Residue 6 is the D-amino acid isomer
<220> FEATURE:
<221> NAME/KEY: VARIANT
<222> LOCATION: (8)..(8)
<223> OTHER INFORMATION: Residue 8 is the D-amino acid isomer

<400> SEQUENCE: 9

Tyr Asp Ser Glu Tyr Glu Ser Glu
1               5

<210> SEQ ID NO 10
<211> LENGTH: 8
<212> TYPE: PRT
<213> ORGANISM: Artificial
<220> FEATURE:
<223> OTHER INFORMATION: Hyaluronan mimicking peptide.
<220> FEATURE:
<221> NAME/KEY: Variant
<222> LOCATION: (6)..(6)
<223> OTHER INFORMATION: Residue 6 is the D-amino acid isomer

<400> SEQUENCE: 10

Tyr Asp Ser Glu Tyr Glu Ser Glu
1               5

<210> SEQ ID NO 11
<211> LENGTH: 6
<212> TYPE: PRT
<213> ORGANISM: Artificial
<220> FEATURE:
<223> OTHER INFORMATION: Hyaluronan mimicking peptide.
<220> FEATURE:
<221> NAME/KEY: REPEAT
<222> LOCATION: (1)..(6)
<223> OTHER INFORMATION: 1 to n possible repeats
<220> FEATURE:
<221> NAME/KEY: misc_feature
<222> LOCATION: (3)..(3)
<223> OTHER INFORMATION: Xaa is "U" selenocysteine

<400> SEQUENCE: 11

Gly Cys Xaa Asn Ala Gly
1               5
```

MODULATION OF RHAMM (CD168) FOR SELECTIVE ADIPOSE TISSUE DEVELOPMENT

CROSS REFERENCE TO RELATED APPLICATIONS

This application is a 371 National Phase of PCT/US2007/085453, filed on Nov. 21, 2007, which claims benefit of and priority to U.S. Provisional Patent Application No. 60/860,606, filed on Nov. 21, 2006, which is hereby incorporated by reference in its entirety. This application also relates to the co-pending International Application, entitled "Rhamm, a Co-Receptor and Its Interactions with Other Receptors in Cancer Cell Motility and the Identification of Cancer Progenitor Cell Populations," which claims priority to U.S. Provisional Patent Application No. 60/860,607, also filed on Nov. 21, 2006, both of which are hereby incorporated by reference in their entirety for all purposes.

REFERENCE TO ATTACHED SEQUENCE LISTING

This application refers to and incorporates by reference the attached sequence listing supplied in paper and computer-readable form, both of which are identical.

STATEMENT OF GOVERNMENTAL SUPPORT

This invention was made with government support under Grant number MOP-57694 awarded by the Canadian Institutes of Health Research (CIHR), under the Breast Cancer Society of Canada Translational Breast Cancer Research Unit, under Grant number DOD-PC050959 awarded by the U.S. Department of Defense, and under Contract No. DE-AC02-05CH11231 awarded by the U.S. Department of Energy. The government has certain rights in this invention.

BACKGROUND OF THE INVENTION

1. Field of the Invention

The present invention relates to the field of tissue reconstruction, repair and development, and more specifically the modulation of Rhamm (CD168) for wound repair and selective adipose tissue development.

2. Related Art

Rhamm is an HA-binding protein that is either poorly or not expressed in most normal adult tissues but is highly expressed in aggressive human tumors (Adamia, S., Maxwell, C. A., and Pilarski, L. M. 2005. Hyaluronan and hyaluronan synthases: potential therapeutic targets in cancer. Curr Drug Targets Cardiovasc Haematol Disord 5:3-14; Tammi, M. I., Day, A. J., and Turley, E. A. 2002. Hyaluronan and homeostasis: a balancing act. J Biol Chem 277:4581-4584; Toole, B. P. 2004. Hyaluronan: from extracellular glue to pericellular cue. Nat Rev Cancer 4:528-539). Rhamm (gene name HMMR) is the Receptor for Hyaluronic Acid Mediated Motility, also known as CD168. Rhamm is a non-integral cell surface (CD168) and intracellular hyaluronan binding protein. Analyses of animal models suggest instructive roles for Rhamm in tumorigenesis and in other disease processes such as arthritis, consistent with its well-documented in vitro functions in migration and proliferation/apoptosis (Turley, E. A., Noble, P. W., and Bourguignon, L. Y. 2002. Signaling properties of hyaluronan receptors. J Biol Chem 277:4589-4592). Although migration and proliferation/apoptosis are essential functions for morphogenesis and tissue homeostasis, genetic deletion of Rhamm does not affect embryogenesis or adult homeostasis (Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). Oncogene 22:6873-6882). In the literature to date, a physiological function for Rhamm has remained elusive.

Rhamm was originally isolated from subconfluent migrating fibroblasts in vitro (Turley, E. A. 1982. Purification of a hyaluronate-binding protein fraction that modifies cell social behavior. Biochem Biophys Res Commun 108:1016-1024) and subsequently cloned from mesenchymal cells (Hardwick, C., Hoare, K., Owens, R., Hohn, H. P., Hook, M., Moore, D., Cripps, V., Austen, L., Nance, D. M., and Turley, E. A. 1992. Molecular cloning of a novel hyaluronan receptor that mediates tumor cell motility. J Cell Biol 117:1343-1350). Since antibodies prepared against a shed form of Rhamm blocked HA-stimulated-fibroblast motility, Rhamm was originally described as a cell surface protein that can transduce motogenic signaling pathways in culture (Turley, E. A., Noble, P. W., and Bourguignon, L. Y. 2002. Signaling properties of hyaluronan receptors. J Biol Chem 277:4589-4592). However, HA-bound Rhamm was later detected in intracellular compartments such as the actin and microtubule cytoskeletons, nucleus and cytoplasm (Adamia, S., Maxwell, C. A., and Pilarski, L. M. 2005. Hyaluronan and hyaluronan synthases: potential therapeutic targets in cancer. Curr Drug Targets Cardiovasc Haematol Disord 5:3-14). More recently, Rhamm has been shown to decorate centrosomes and mitotic spindles. Rhamm is required for mitotic spindle formation in culture and acts on the BRCA1/BARD1 pathway to regulate mitotic spindle integrity (Joukov et al., Cancer Cell, 2006: 127:539-52). Collectively, these results suggest that Rhamm may have both extracellular and intracellular functions, (Nickel, W. 2005. Unconventional secretory routes: direct protein export across the plasma membrane of mammalian cells. Traffic 6:607-614; Samuel, S. K., Hurta, R. A., Spearman, M. A., Wright, J. A., Turley, E. A., and Greenberg, A. H. 1993. TGF-beta 1 stimulation of cell locomotion utilizes the hyaluronan receptor RHAMM and hyaluronan. J Cell Biol 123:749-758; Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348) thus resembling a group of proteins including epimorphin/syntaxin-2 and autocrine motility factor/phosphoglucose isomerase that are also found at the cell surface where they transmit signals across the cell membrane even though, like Rhamm, they lack both golgi-ER export peptides and membrane spanning sequences (Nickel, W. 2005. Unconventional secretory routes: direct protein export across the plasma membrane of mammalian cells. Traffic 6:607-614).

Although the intracellular vs. extracellular functions of Rhamm have not yet been clearly dissected, accumulating data suggest that both forms may contribute to mesenchymal phenotypes, at least during disease. For example, Rhamm expression in culture is increased in transformed fibroblasts by fibrogenic cytokines such as TGF-β (Samuel, S. K., Hurta, R. A., Spearman, M. A., Wright, J. A., Turley, E. A., and Greenberg, A. H. 1993. TGF-beta 1 stimulation of cell locomotion utilizes the hyaluronan receptor RHAMM and hyaluronan. J Cell Biol 123:749-758) and cell surface Rhamm is required for activation through fibrogenic cytokines such as PDGF (Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348). Furthermore, we have shown that Rhamm expression is high in clinically aggressive mesenchymal tumors (fibromatoses or desmoid tumors) (See Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). *Oncogene* 22:6873-6882). Also in a mouse model susceptible to desmoid and upper intestinal tract tumors, genetic deletion of Rhamm strongly reduces desmoid initiation and invasion but not upper intestinal tract tumors. Fibroproliferative processes such as aggressive fibromatosis resemble proliferative/migratory stages of wound healing (Cheon, S. S., Cheah, A. Y., Turley, S., Nadesan, P., Poon, R., Clevers, H., and Alman, B. A. 2002. beta-Catenin stabilization dysregulates mesenchymal cell proliferation, motility, and invasiveness and causes aggressive fibromatosis and hyperplastic cutaneous wounds. Proc Natl Acad Sci USA 99:6973-6978). Furthermore, the expression of Rhamm is modulated during wounding (Lovvorn, H. N., 3rd, Cass, D. L., Sylvester, K. G., Yang, E. Y., Crombleholme, T. M., Adzick, N. S., and Savani, R. C. 1998. Hyaluronan receptor expression increases in fetal excisional skin wounds and correlates with fibroplasia. J Pediatr Surg 33:1062-1069; discussion 1069-1070).

It has been found that factors that regulate fibroblast function play dual roles in wound repair and tumorigenesis (Bissell, D. M. 2001. Chronic liver injury, TGF-beta, and cancer. Exp Mol Med 33:179-190; Park, C. C., Bissell, M. J., and Barcellos-Hoff, M. H. 2000. The influence of the microenvironment on the malignant phenotype. Mol Med Today 6:324-329). Others have recently begun to study mesenchymal stem cell trafficking/differentiation into wound sites. (See Li H, et al., 2006 Adult bone-marrow-derived mesenchymal stem cells contribute to wound healing of skin appendages. *Cell Tissue Res*, Epub ahead of publication; Fu X, et al., 2006 Enhanced wound-healing quality with bone marrow mesenchymal stem cells autografting after skin injury. *Wound Repair Regen.* 14: 325-35; Mansilla E., et al., 2006 Bloodstream cells phenotypically identifical to human mesenchymal bone marrow stem cells circulate in large amounts under the influence of acute large skin damage: new evidence for their use in regenerative medicine. *Transplant Proc.* 38: 967-9; Shumakov VI, 2003 Mesenchymal bone marrow stem cells more effectively stimulate regeneration of deep burn wounds than embryonic fibroblasts. *Bull Exp Biol Med* 136: 192-5.) Mesenchymal stem cells and resident fibroblasts in wounds have immune-modulatory functions that affect the timing and extent of fibrosis during wound repair (Domaszewska A, and Oszewski W L 2006 Ann. Transpint. 11:45-52).

SUMMARY OF THE INVENTION

The present invention describes the use of Rhamm as a fibrogenic factor required for appropriate cueing of migration and differentiation of mesenchymal stem cells which are necessary for various functions including wound repair, cartilage and bone formation, adipogenesis, muscle formation, and regulation of tissue injuries such as heart attacks and stroke injuries. Herein is described the modulation of Rhamm expression to affect Rhamm function and thereby to increase or decrease the rate of fibrotic wound response, depending upon the desired response, and in some embodiments, to selectively enhance adipogenesis.

A method for selectively enhancing subcutaneous adipose tissue development in a subject, the method comprising administering a compound that blocks Rhamm function to the subject, whereby adipocyte formation occurs in dermal fibroblasts and volume is added in a selected subcutaneous area in the subject. In another embodiment, a method for selectively inhibiting visceral adipose tissue formation in a subject, the method comprising administering a compound that blocks Rhamm function to the subject, thereby selectively inhibiting visceral adipose tissue formation in the subject.

In one embodiment, the compound that blocks Rhamm or Rhamm/hyaluronan function is an antibody that specifically binds Rhamm, a soluble recombinant Rhamm protein fragment, a peptide mimetic, a siRNA, an antisense oligonucleotide, or an aptamer. In some embodiments, the Rhamm function that is blocked is Rhamm binding to CD44. In one embodiment, the compound is a Rhamm peptide mimetic. In an exemplary embodiment, the Rhamm peptide mimetic is substantially homologous to SEQ ID No:5.

In one embodiment, an effective therapeutic amount of the anti-Rhamm compound in freeze-dried or liquid formulation is drawn into a syringe at a fixed dosage. Other dose dilutions are possible. Injections are made in multiple locations through the selected region of the body. Topical anesthetics such as 4% lidocaine cream or cetacaine spray may be used to reduce the discomfort of the procedure. Topical antibiotics may also be used to reduce the risk of infection. In further embodiments, about 5 to about 2000 LD 50 units of the anti-Rhamm compound are administered to said subject.

In some embodiments, the subject is a mammal. In a preferred embodiment, the subject is a patient. In one embodiment, the present invention is reconstruction of a patient's tissues, including but not limited to breast (e.g. after surgery to remove tumors), face or limb (e.g. after car accident or burning). For such uses, Rhamm compounds are optionally used in conjunction with tissue grafting material or other procedures that enhance youthful skin or repair of damaged tissues. In some embodiments, the subject has been diagnosed with a cardiovascular disease, diabetes, or an obesity-related disease.

In one embodiment, the present invention provides a method of modulating Rhamm to promote wound repair and contraction in an injured subject, comprising the steps of: providing a compound that enhances Rhamm function, administering the compound to the wounded area of a subject, whereby rate of wound contraction is increased. In another embodiment, a method of modulating Rhamm to promote muscle differentiation, comprising the steps of: providing a compound that enhances Rhamm function, administering said compound to a selected area of a subject, whereby muscle differentiation occurs more rapidly. And in another embodiment, a method of modulating Rhamm to promote bone density, comprising the steps of: providing a compound that enhances Rhamm function, administering a compound that enhances Rhamm activity to a subject, whereby bone formation and density increases. In an exemplary embodiment wherein the compound that is provided enhances Rhamm activity, the compound can be Rhamm agonist antibodies, HA mimetics, or a Rhamm cDNA. In one embodiment, the compound is an HA mimetic

Figure 2:
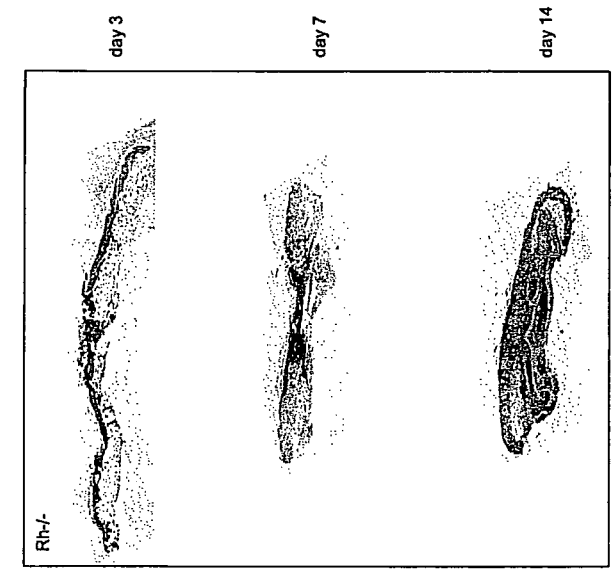
Figure 2:
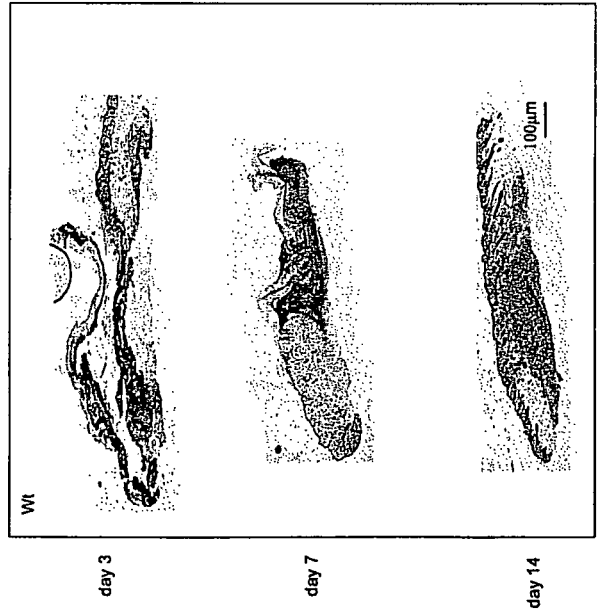
Figure 2:
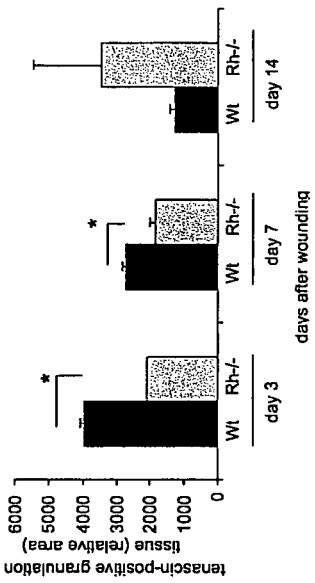

FIG. 2. Loss of Rhamm delays and alters the pattern of granulation tissue formation in skin wounds. A: Tenascin protein expression in wound sections: Wound granulation tissue is abundant in day 7 Wt wounds as indicated by positive and homogenous staining for tenascin. Granulation tissue has largely resolved in Wt wounds by day 14 as indicated by restricted tenascin staining The area of tenascin-positive Rh-/- granulation tissue is less in days 3 and 7 than Wt and has become aberrantly "patchy" by day 14, indicating delayed and abnormal patterning of granulation tissue resolution. The scale bar represents 100 µm. B: Areas of tenascin-positive granulation tissue: The area of Wt granulation tissue is significantly greater than Rh-/- at both day 3 and 7 after wounding ($p<0.01$ for both time points). High standard errors of tenascin-positive areas of Rh-/- granulation tissue reflect aberrant resolution patterns. Values represent the Mean and S.E.M. N=4 tissue sections from 8 male mice for each genotype.

Figure 3:
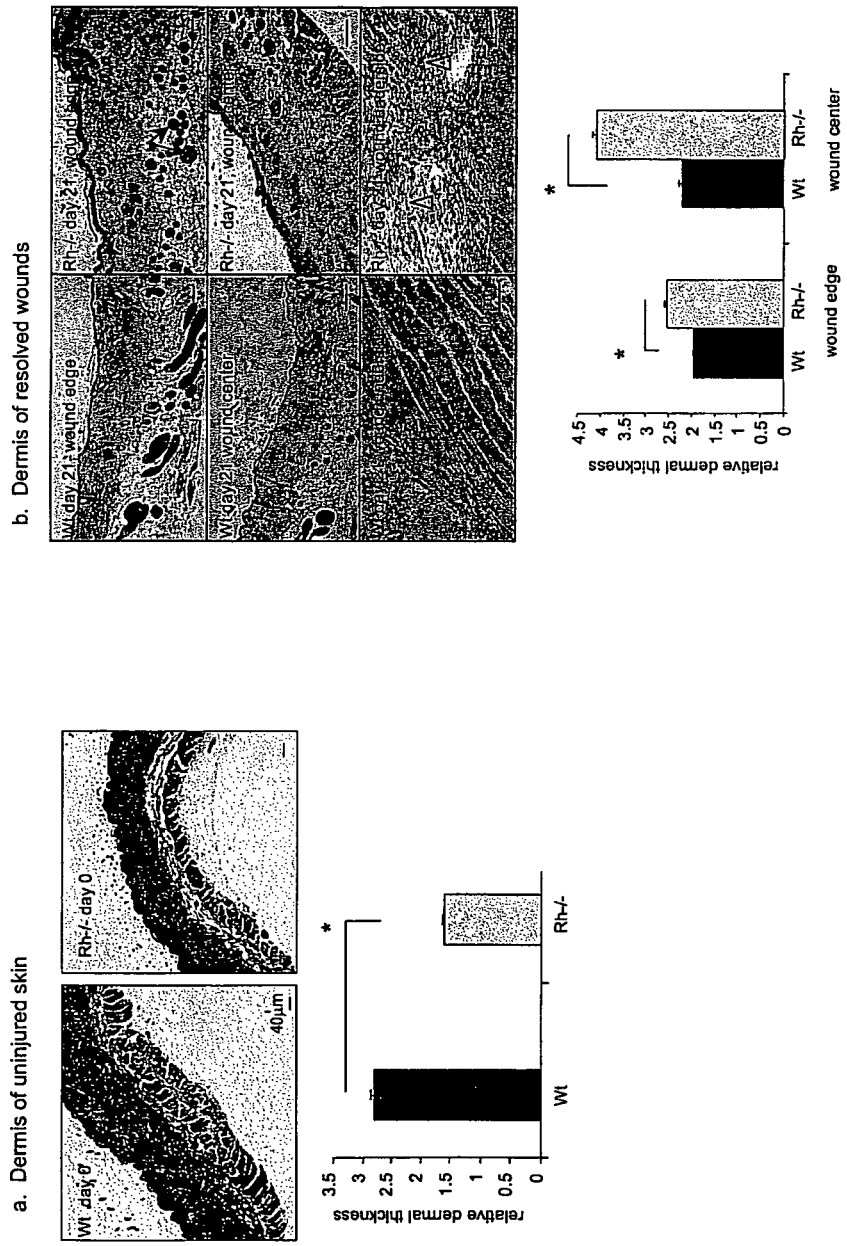

FIG. 3. Loss of Rhamm expression results in aberrant dermal structure and thickness in both uninjured and repaired skin. A: Dermis of resolved wounds: The histology of the dermis at both the center and edges of Wt wounds at day 21 are similar, suggesting that the wound has resolved. Day 21 Wt dermis is also significantly thinner than Rh-/- wounds ($p<0.0001$ and $p<0.01$) suggesting that Rh-/- wounds have not yet fully resolved. This is also suggested by the aberrant dermal differentiation (e.g. hair follicles have not formed shafts, subcutaneous lipid layer is aberrant and muscle layer is not yet continuous at the underside of wounds). Solid arrowheads mark the still discernable wound site in Rh-/- skin. Solid arrows mark undifferentiated hair follicles and open arrowheads mark incomplete muscle formation observed at the underside of Rh-/- wounds. Scale bars represent 200 µm. B: Dermis of uninjured skin: The dermis of uninjured Wt skin (day 0) is significantly thicker than uninjured Rh-/- skin ($p<0.0001$). Sections were stained with Masson's Trichrome and hematoxylin/eosin. Scale bars represent 40 µm. Masson's trichrome stains dermal collagen green and hematoxylin/eosin stains cells red. Values represent the Mean and S.E.M. of 5 areas from 3 separate tissue sections for each experimental condition.

Figure 4:
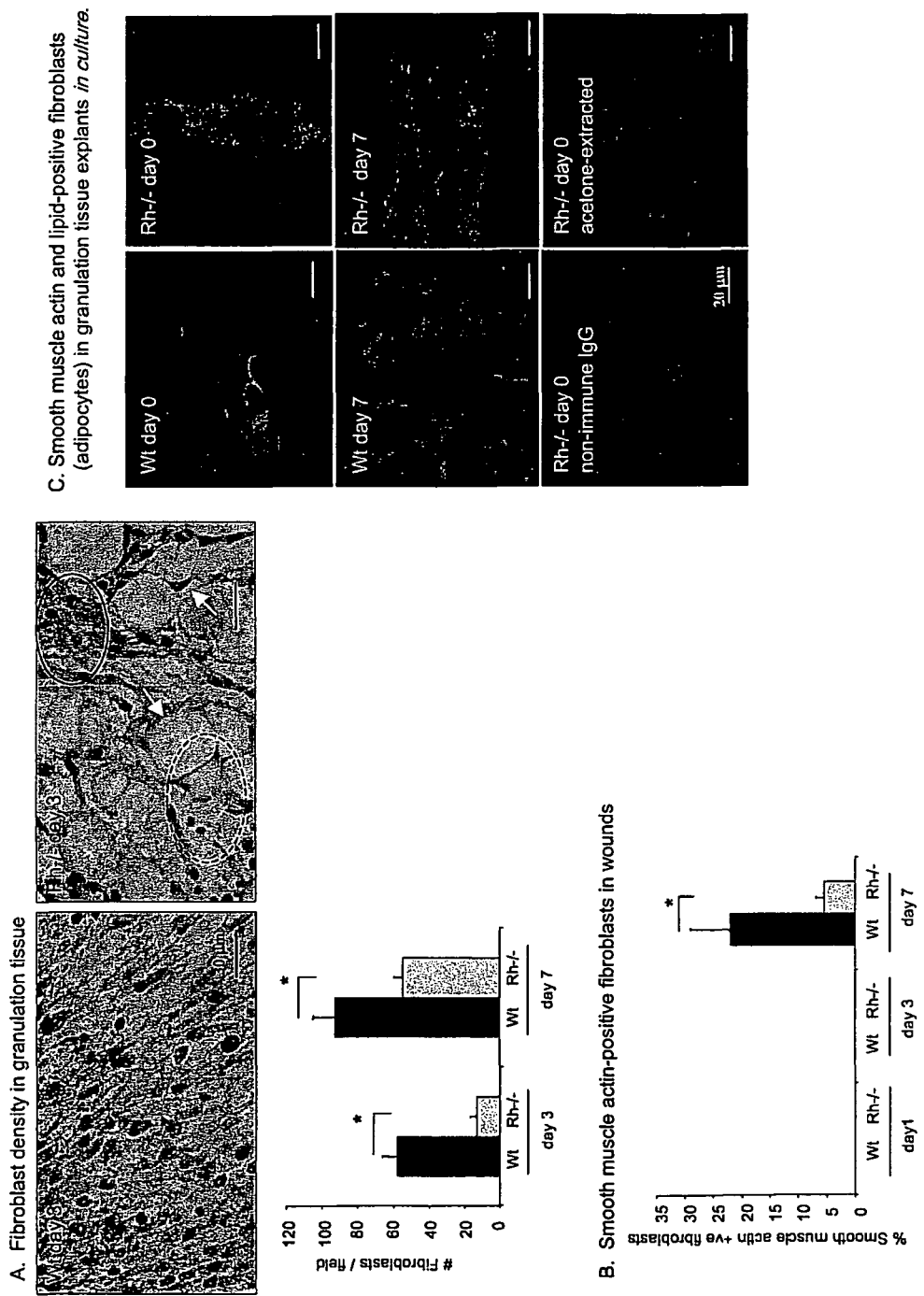

FIG. 4. Loss of Rhamm reduces fibroblast density and increases granulation tissue cell heterogeneity. A: Fibroblast Density in granulation tissue: The averaged density of fibroblasts/field is significantly reduced in Rh-/- granulation tissue at both day 3 ($p<0.0001$) and 7 ($p<0.001$) after wounding. Arrows indicate the presence of vacuolated adipocytes. Fibroblast density is heterogeneous in Rh-/- granulation tissue (e.g. dotted circle is sparse; filled line circle is dense). Values in graphs represent the Mean and S.E.M., N=4 sections from 8 animals for each genotype. Scale bars represent 30 µm. B: Smooth muscle actin-positive fibroblasts in wounds: The number of wound smooth muscle actin-positive myofibroblasts is significantly reduced in day 7 Rh-/- wounds compared to Wt granulation tissue ($p<0.0001$). Values in graphs represent the Mean and S.E.M., N=4 sections from 8 animals for each genotype. C: Smooth muscle actin- and lipid-positive fibroblasts (adipocytes) in granulation tissue explants in culture: smooth muscle actin-positive fibroblasts are significantly reduced while lipid-positive cells are significantly increased in Rh-/- vs. Wt granulation tissue explants ($p<0.0001$). In confocal images, red staining is smooth muscle actin and green staining is BODIPY493/503 taken up into lipid droplets within cells. Scale bars represent 20 µm.

Figure 5:
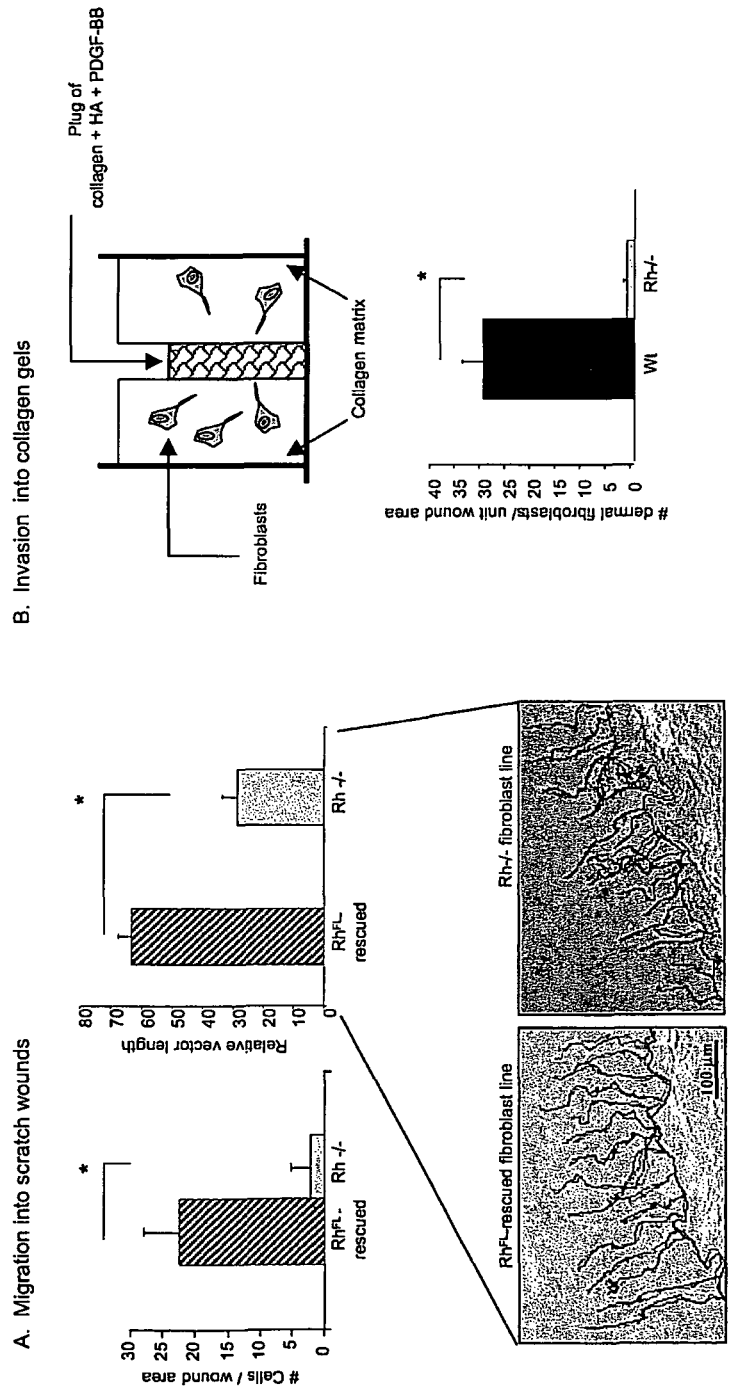

FIG. 5. Loss of Rhamm reduces fibroblast migration and invasion. A: Migration into scratch wounds: Transfection of immortalized Rh-/- fibroblasts with $Rh^{FL}$ cDNA restores their ability to efficiently migrate into 3 mm scratch wounds in response to PDGF-BB; significantly more $Rh^{FL}$-rescued fibroblasts migrate into the wound gap than Rh-/- fibroblasts ($p<0.0001$). Values represent the Mean and S.E.M., N=6 randomly chosen fields. Time-lapse analysis of wound edges shows that re-expression of $Rh^{FL}$ permits Rh-/- fibroblasts to migrate longer distances over a 24 hr period. The scale bar represents 100 µm. Values represent the Mean and S.E.M. N=3 experiments. B: Invasion into collagen gels: Diagram shows the construction of a collagen gel invasion assay where HA and PDGF-BB is present only in the central plug. A significantly greater number of Wt dermal fibroblasts migrate into gel centers than do Rh-/- dermal fibroblasts ($p<0.00001$). Values represent the Mean and S.E.M., N=4 experiments.

Figure 6:
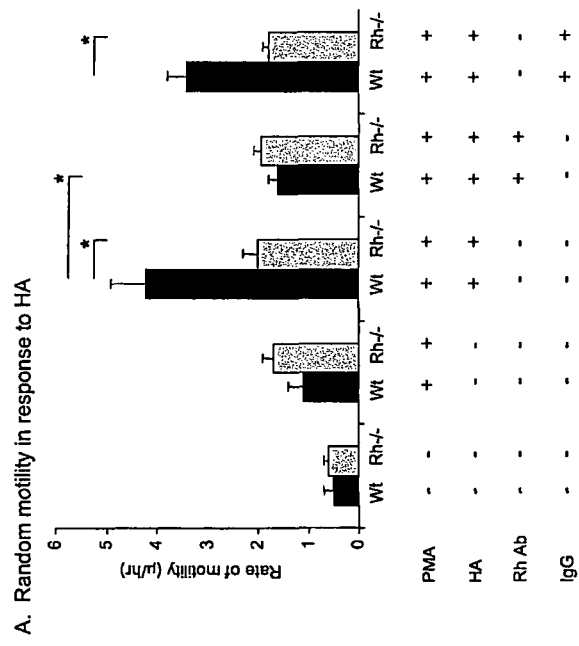
Figure 6:
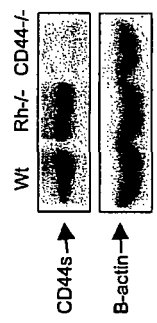

FIG. 6. Loss of Rhamm ablates migration of fibroblasts in response to HA. A: Random motility in response to HA: In contrast to Wt, Rh-/- fibroblasts do not increase random motility in response to HA. Rhamm antibodies reduce motility of Wt but not Rh-/- fibroblasts in the presence of HA. The values represent the Mean and S.E.M., N=30 cells and are the results of one of 4 similar experiments. B: CD44 protein expression: Rh-/-fibroblasts express similar levels of CD44 proteins as Wt, assessed by western blot analysis. β-actin is used as a protein loading control.

Figure 7:
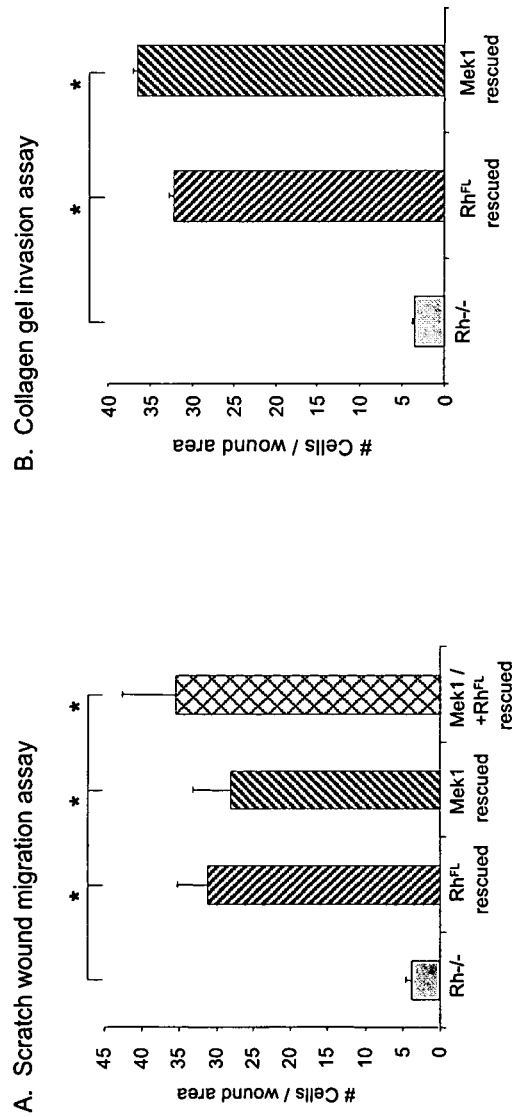

FIG. 7. Mutant active Mek1 rescues migration and invasion defects in Rhamm-/- fibroblasts. A: Scratch wound migration assay: Expression of mutant active Mek1 in Rh-/- fibroblasts restores their ability to migrate into a 3 mm wound gap in response to PDGF-BB to a similar extent as expression of full-length Rhamm. Co-expression of Mek1 and $Rh^{FL}$ has no additive effect on migration. Asterisks indicate $p<0.01$. Values represent the Mean and S.E.M., N=3 experiments. B: Collagen gel invasion assay: Expression of mutant active Mek1 in Rh-/- fibroblasts rescues the ability of Rh-/- fibroblasts to invade into collagen gel centers (see FIG. 7B) to a similar extent as expression of $Rh^{FL}$. Asterisks indicate $p<0.00001$. Values represent the Mean and S.E.M., N=3 experiments.

Figure 8:
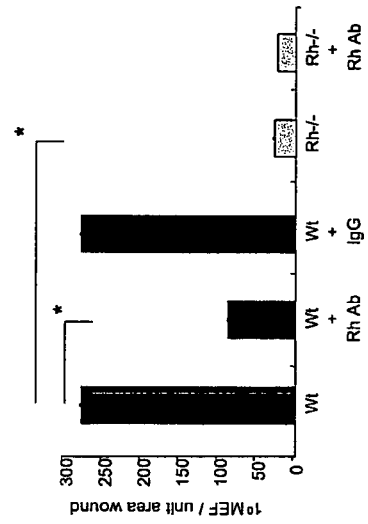
Figure 8:
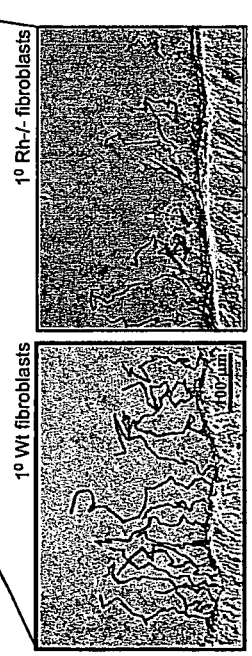
Figure 8:
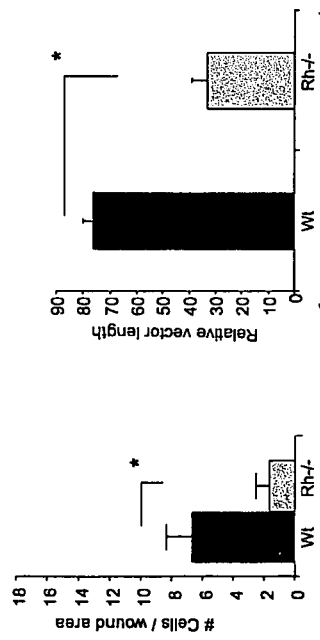

FIG. 8. Loss of Rhamm reduces migration and invasion of primary fibroblasts. A: Migration into Scratch wounds: Significantly more Wt fibroblasts migrate into wound gaps than Rh-/- fibroblasts ($p<0.0001$). Values represent the Mean and S.E.M., N=6 randomly chosen areas. Time-lapse analysis of wound edges shows that Wt fibroblasts migrate longer distances than Rh-/- fibroblasts over a 24 hr period ($p<0.0001$). The scale bar represents 100 µm. Values represent the Mean and S.E.M., N=3 experiments. B: Invasion into collagen gels: A significantly greater number of Wt fibroblasts invade into the center of collagen gels than Rh-/- fibroblasts ($p<0.00001$). Furthermore, anti-Rhamm antibodies significantly block invasion of Wt fibroblasts ($p<0.00001$) but not Rh-/- fibroblasts. Non-immune IgG was used as a control for the anti-Rhamm antibody. Values represent the Mean and S.E.M., N=4 experiments.

Figure 9:
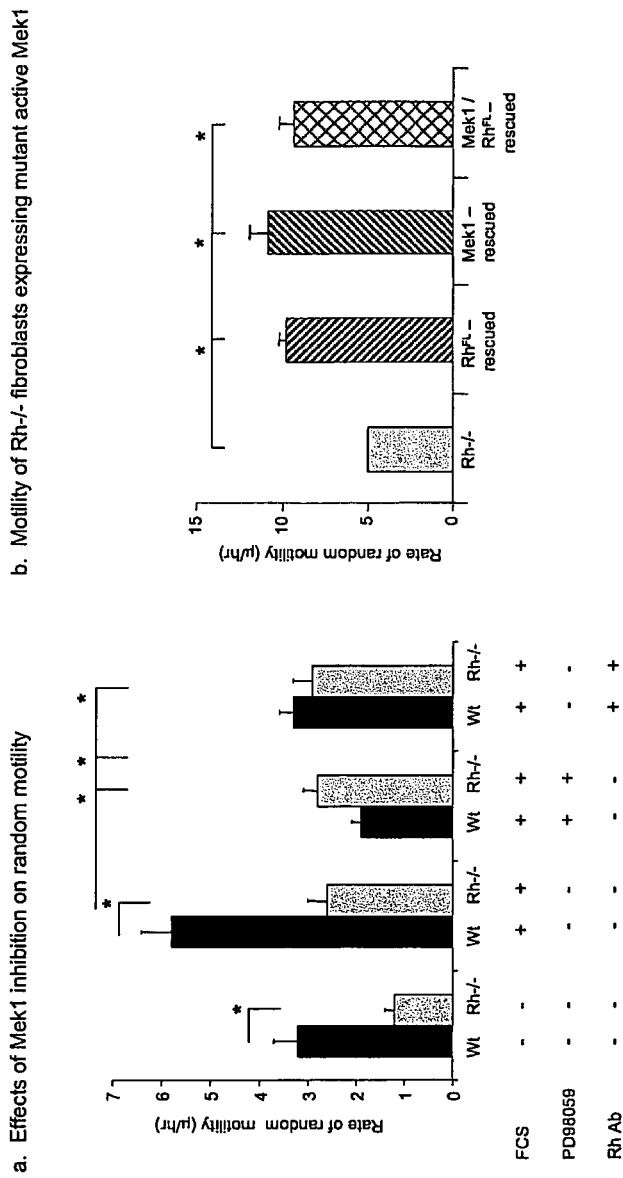

FIG. 9. ERK1,2 activity is required for a motogenic response to PDGF-BB and mutant active Mek1 rescues the motogenic defect of Rhamm-/- fibroblasts. A: Effects of active Mek1 inhibition on random motility: Primary Wt fibroblasts increase random motility in response to FCS to a significantly greater extent than litter-matched Rh-/- fibroblasts.

The Mek1 inhibitor, PD98059, and anti-Rhamm antibodies significantly reduce motility of Wt (but not Rh-/- fibroblasts) in the presence of FCS. Asterisks denote significance levels of p<0.0001. The values represent the Mean and S.E.M., N=30 cells and are the results of one of 4 similar experiments. B: Motility of Rh-/- fibroblasts expressing mutant active Mek1: Random motility of Rh-/- fibroblasts is significantly increased by either expression of Rh$^{FL}$ or mutant active Mek1 (p<0.0001). Co-expression of Rh$^{FL}$ and mutant active Mek1 does not further increase cell motility. Values represent the Mean and S.E.M., N=30 cells/treatment.

Figure 10:
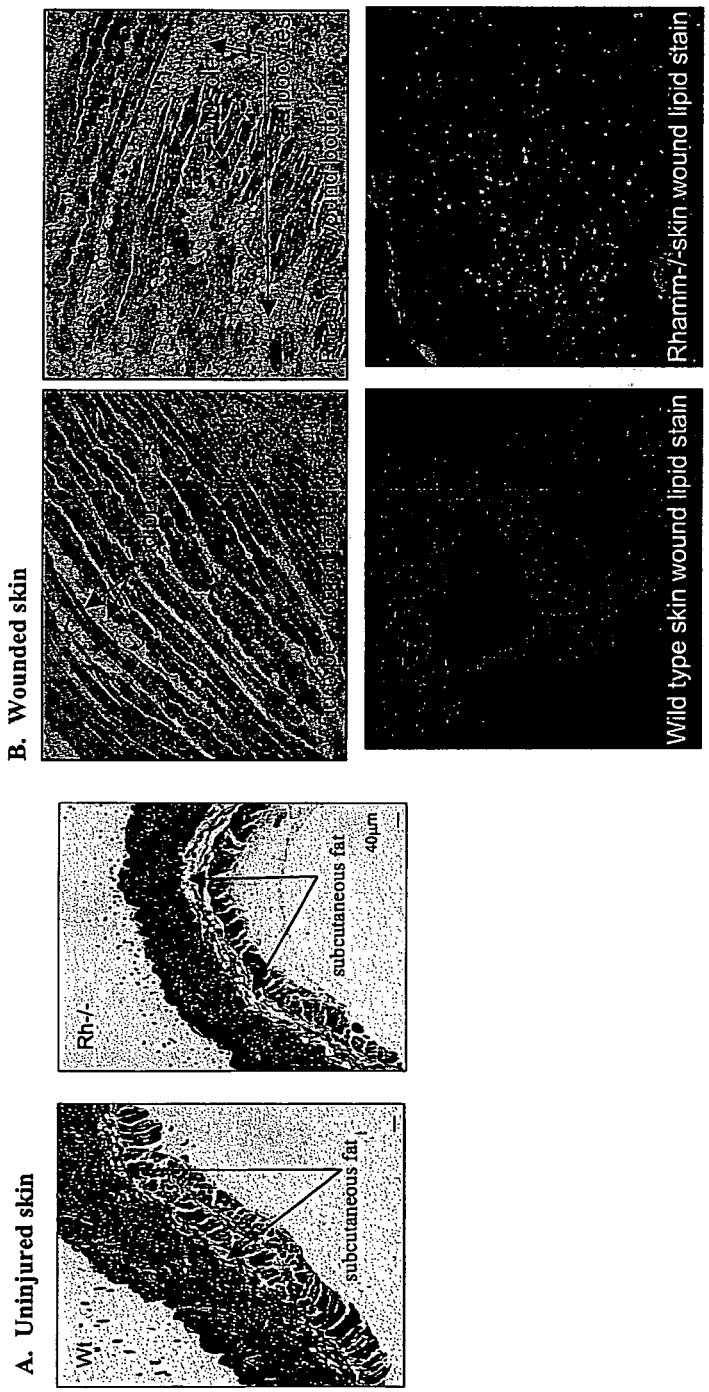
Figure 10:
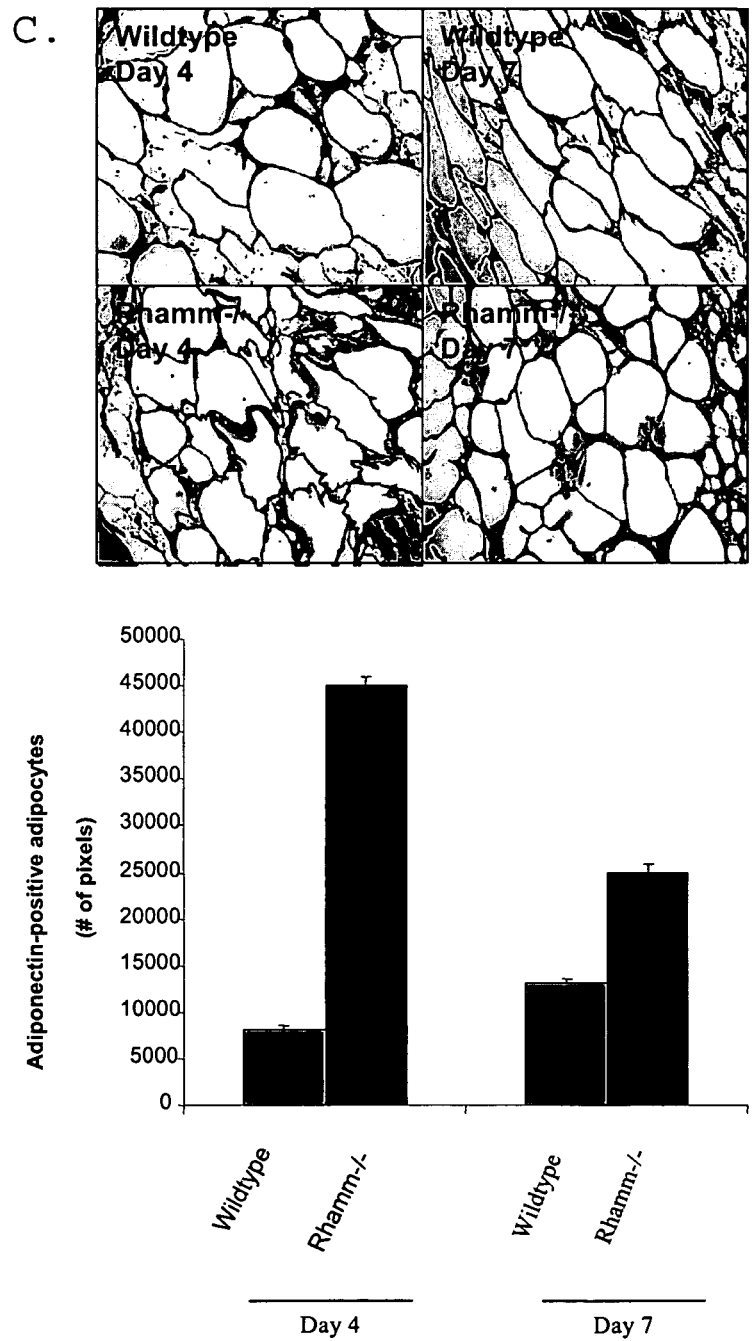

FIG. 10. Subcutaneous Adipogenesis is increased in both uninjured and excisionally wounded Rhamm-/-skin. A: The subcutaneous layer of adipocytes is thicker in uninjured Rh-/- skin than in litter-matched, gender matched (male) skin. Adipocytes were identified by their location in the skin and by the presence of large vacuoles. Paraffin processed sections were stained with Mason's trichrome. B: The subcutaneous adipocyte layer is also increased after wounding in Rhamm-/- skin vs. litter matched, age and gender matched (6mos-1year, 1 year shown, males shown) mice. The upper panel shows images of paraffin processed tissue sections taken at the bottom of the wounds near the muscle and adipocyte layer. The sections were stained with hematoxylin and adipocytes are identified as vacuolated cells. The bottom panel are images of frozen sections cut through wounds and stained with bodipy, which is a lipophilic dye used to identify triglycerides in fat vacuoles.

C. The upper panel shows high magnification (40× objective) images of paraffin processed tissue sections taken from a section cut vertically through wildtype and Rhamm-f/- wound sites. The sections were stained with hematoxylin and also with anti-adiponectin, an adipocyte specific gene expressed by subcutaneous and visceral fat adipocytes. Adipocytes, which have large vacuoles stain positively for adiponectin. The lower panel shows quantification of adiponectin staining in wildtype and Rhamm-/- wounds. Rhamm-/- wounds express higher levels of adiponectin than wildtype wounds.

Figure 11:
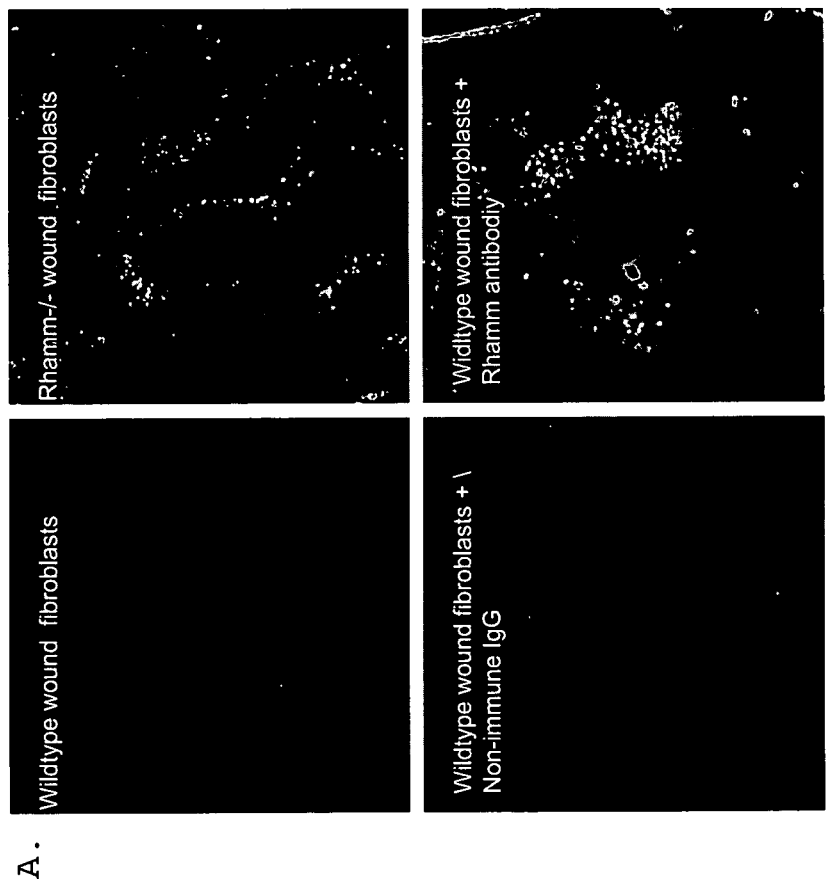
Figure 11:
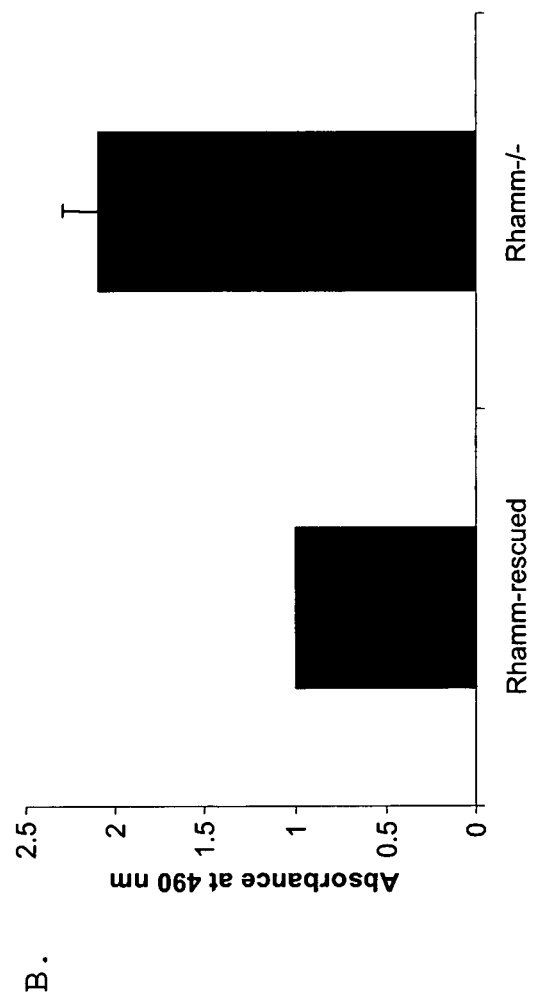

FIG. 11. Genetic loss of Rhamm and anti-Rhamm antibodies both increase adipogenesis. A. Wound fibroblasts were grown from explanted Wt and Rhamm-/-Day 0-7 excisional wound punches in 2D culture in DMEM+10% FCS. Wild-type wound fibroblasts were exposed to non-immune IgG or anti-Rhamm IgG antibody for 4 days. Cells were stained with Bodipy to detect lipid droplets, are seen as green fluorescence.

B. Rhamm-/- and Rhamm-rescued dermal fibroblasts isolated from uninjured skin and immortalized in culture were assessed for their adipogenic potential by exposure to culture medium that promotes adipogenesis. Cells were cultured in DMEM+10% FCS for 7 days then maintained in adiogenic medium for 21 days, which consisted of DMEM+10% FCS supplemented with 0.5 uM dexamthasone, 0.5 mM isobutyl-methylxanthine, 10 ug/ml insulin and 200 uM indomethacin (Sekiya I, et al., 2004 J Bone Mineral Res. 19: 256-264). Cultures were fixed in 10% formalin for 1 hr at 4° C. then stained with Oil Red O. Staining was quantified by absorbance at 490 nm. The graph shows increased Oil Red O staining in Rhamm-/- dermal fibroblasts compared to Rhamm-rescued dermal fibroblasts.

Figure 12:
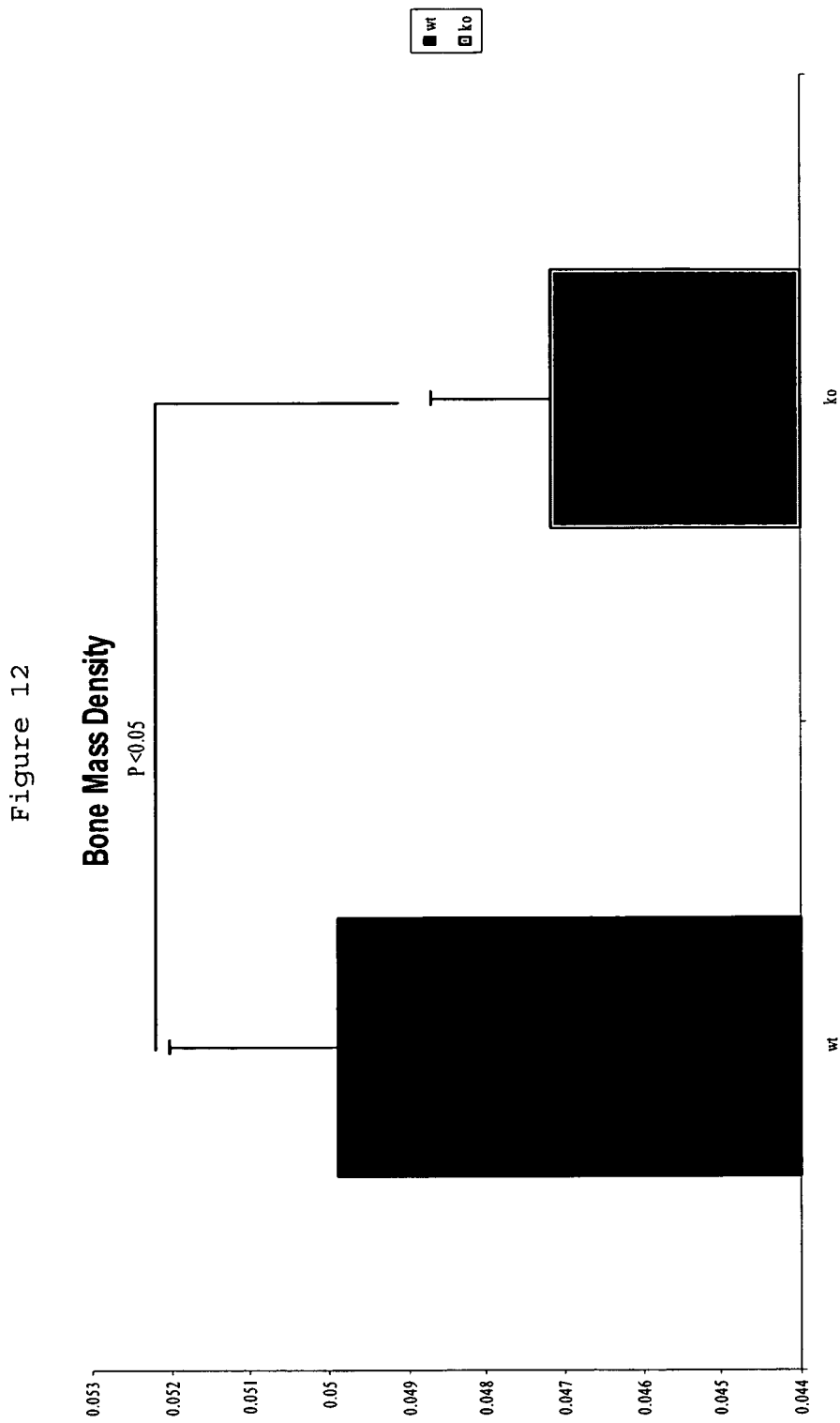

FIG. 12. The Bone Density of Wild-type (Wt) and Rhamm-/- (ko) mice. Male and female Wt and ko mice were assessed for bone density using image analysis. The bone density of Wt mice is significantly greater (P<0.05, Student's "T" test) than ko mice indicating that loss of Rhamm results in decreased bone density. Values are the mean and S.E.M. Wt n=5 mice; ko n=8 mice.

Figure 13:
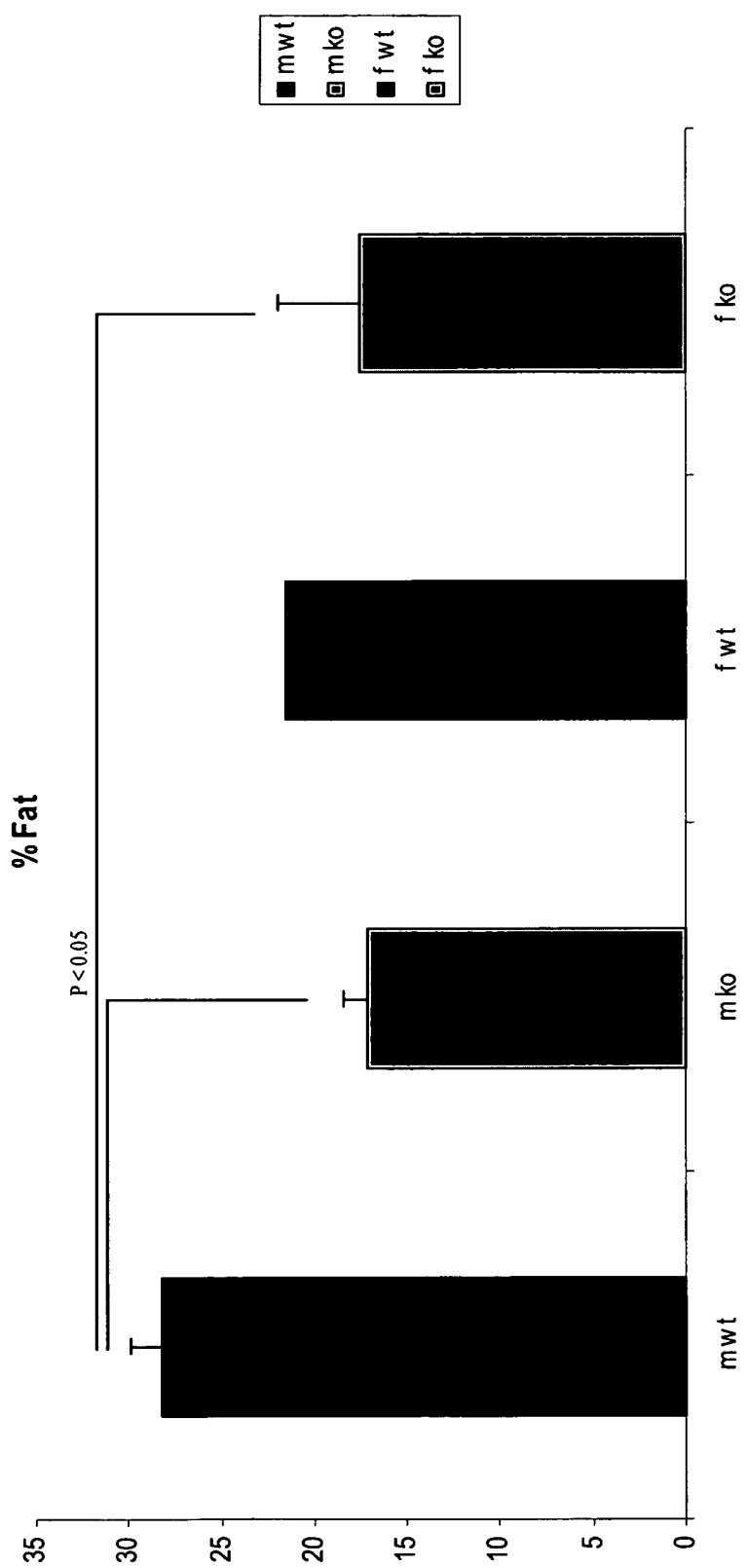

FIG. 13. Visceral fat deposition in Wild-type (Wt) and Rhamm-/- (ko) mice. Visceral fat was determined by image analysis and calculated as % fat deposition. Visceral fat deposition is significantly less in Wt than in ko mice. Statistical significance (P<0.05, Student's "T" test) was achieved with male mice because of the larger number used for this study. Values represent the Mean and S.E.M. Wt males n=4; females n=1; ko males n=4, females n=4.

Figure 14:
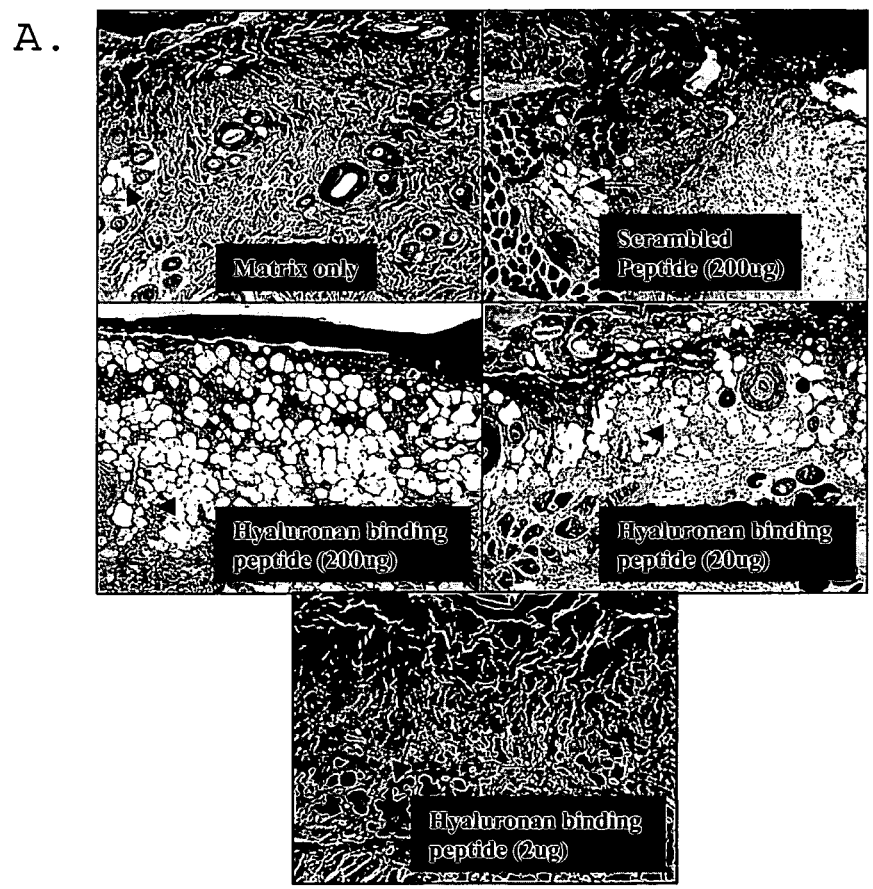
Figure 14:

FIG. 14. Effect of a hyaluronan binding peptide on wound site (sub-cutaneous) adipogenesis. A. Full thickness excisional wounds were placed on the flanks of male Fisher rats then these were covered with collagen gels (matrix) containing either no peptide (matrix), hyaluronan binding peptide (at 200, 20 and 2 ug/woundsite) or scrambled peptide (at 200 ug/woundsite). The wound sites were excised 14 days after wounding and processed for histology. Micrographs show Mason Trichrome stained tissue sections through the center of the wounds. Hyaluronan binding peptide-treated wound sites filled with adipocytes as indicated by vacuolated appearance of the wounds (arrows indicate adipocytes).

B. Hyaluronan binding peptide increases subcutaneous fat after injection into uninjured skin. 0.2, 2 and 20 ug of hyaluronan binding peptide or scrambled peptide were mixed in 1 ml of type 1 collagen solution, (3 mg/m1) and 0.25 ml of the solution was injected under the skin on the flanks of 3 month old male Fisher rats. Hair at the site of injection was removed prior to injection using Nair for marking purposes. Injection sites were harvested by skin punches at 4, 7 and 14 days after injection. Micrographs show accumulation of adipcytes, detected by vacuoles, at the sites where the hyaluronan binding peptide was injected but not where the scrambled peptide control was injected.

DETAILED DESCRIPTION OF THE INVENTION

I. Introduction

The present invention provides a method for selectively enhancing subcutaneous adipose tissue development in a subject. The present invention also provides a method for selectively inhibiting visceral adipose tissue formation in a subject.

The present invention is based on our results identifying Rhamm as a fibrogenic factor required for appropriate cueing of migration/differentiation necessary for repair, and as an essential regulator of ERK1,2 motogenic-signaling pathways required for wound repair.

II. Abbreviations and Definitions

"2D" 2-dimensional culture
"3D" 3-dimensional culture
"bFGF-2" Basic fibroblast growth factor-2
"CD44" is an integral hyaluronan receptor that can either promote or inhibit motogenic signaling in tumor cells.
"CD168" another name for Rhamm
"ECM" Extracellular matrix
"ERK1,2" Extracellular regulated kinase 1,2
"FAK" Focal adhesion kinase
"HA" Hyaluronic acid/Hyaluronan
"Matrigel" Basement membrane matrix
"MEFs" Mouse embryonic fibroblasts
"Mek1" Mitogen activated kinase kinase 1; an ERK1,2 kinase activator "MMPs" Matrix metalloproteinases "Motogen," a factor that increases the motility of cancer cells.

"MW" Molecular weight

"MW$_{avg}$" Average molecular weight

"PDGF-BB" Platelet derived growth factor-BB

"PDGFR" Platelet derived growth factor receptor

"PMNs" polymorphonuclear cells

"Rhamm" Receptor for Hyaluronic Acid Mediated Motility, also known as CD168. Rhamm is a non-integral cell surface (CD168) and intracellular hyaluronan binding protein that promotes cell motility in vitro and whose expression is strongly upregulated in aggressive tumors.

"Rh$^{Fl}$" Full-length Rhamm

"Rh-/-" Rhamm-/-

"TE" Tris-EDTA

"TGF-β" Transforming growth factor-β

"TGF-βR" Transforming growth factor-β receptor

"Wt" Wild-type

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The phrase "selectively hybridizes to" or "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 6C, with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

It is contemplated that the sequences described herein may be varied to result in substantially homologous sequences which retain the same function as the original. As used herein, a polynucleotide or fragment thereof is "substantially homologous" (or "substantially similar") to another if, when optimally aligned (with appropriate nucleotide insertions or deletions) with the other polynucleotide (or its complementary strand), using an alignment program such as BLASTN (Altschul et al. (1990) J. Mol. Biol. 215:403-410), and there is nucleotide sequence identity in at least about 80%, preferably at least about 90%, and more preferably at least about 95-98% of the nucleotide bases.

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The term, "anti-Rhamm compounds" refers to compounds which can modulate Rhamm expression by either binding to Rhamm or to Rhamm co-factors and thereby modulating Rhamm expression and function.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of ÿ-sheet and ÿ-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 5 can be made detectable, e.g., by incorporating a radiolabel into the peptide, and used to detect antibodies specifically reactive with the peptide).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as Helix 1, 6, 7, 9, or 10 of Apo A-I), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to the chimeric protein of the present invention or portions thereof, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to," refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

II. Rhamm and its Role in Wound Repair, Muscle Differentiation and Bone Density Rhamm is a hyaluronan (HA) binding protein with limited expression in normal tissues and high expression in advanced cancers. We have identified a physiological function for Rhamm during excisional skin wound repair. Genetic deletion of Rhamm impairs wound contraction and granulation tissue formation/resolution. This is associated with enhanced inflammation, sparse fibroplasia and aberrant differentiation as indicated by reduced myofibroblast conversion and increased subcutaneous adipocyte accumulation.

Sparse fibroplasia is associated with an inability of Rhamm-/- (Rh-/-) fibroblasts to resurface large (>3mm) scratch wounds and invade HA-supplemented ECM gels to the extent of wild-type or Rhamm-rescued fibroblasts. These effects result from altered activation kinetics and subcellular targeting of ERK1,2 since stable introduction of constitutively active Mek1 rescues these motogenic defects in Rh-/- fibroblasts.

The results disclosed for the first time herein identify Rhamm as a fibrogenic factor required for appropriate cueing of migration/differentiation necessary for repair, and as an essential regulator of ERK1,2 motogenic-signaling pathways required for wound repair.

The effect of Rhamm loss is disruption of Rhamm/CD44 interactions in mesenchymal and epidermal stem cells. We assessed loss of Rhamm expression for its effect on wound repair, and migration of fibroblasts into wounds. While investigating the effects of Rhamm on wound repair using a mouse strain in which Rhamm has been genetically deleted but in which CD44 expression is unaffected, it was observed that the wounds were filled with adipocytes, while wild-type wounds were not; Rhamm-/- wounds failed to accumulate myofibroblasts while wild-type wounds displayed abundant myofibroblasts.

Since Rhamm is a hyaluronan binding protein and since hyaluronan-Rhamm interactions may contribute to wound repair, we also assessed the effects of a hyaluronan binding peptide on adipogenesis during wounding using a rat model. Hyaluronan binding peptides promoted adipogenesis within the wound site and in uninjured skin indicating that Rhamm: hyaluronan interactions are involved in regulating adipogenesis.

We describe herein the dominant effect of Rhamm loss on granulation tissue fibroblast and polymorphonuclear cell accumulation. Consistent with Rhamm acting as a mesenchymal factor, the consequences of Rhamm loss to wound repair closely resembles that of another mesenchymal protein, vimentin, which is also predominantly expressed in fibroblasts and cells of hematopoietic lineage (Adamia, S., Maxwell, C. A., and Pilarski, L. M. 2005. Hyaluronan and hyaluronan synthases: potential therapeutic targets in cancer. Curr Drug Targets Cardiovasc Haematol Disord 5:3-14; Turley, E. A., Noble, P. W., and Bourguignon, L. Y. 2002. Signaling properties of hyaluronan receptors. J Biol Chem 277:4589-4592; and Eckes, B., Colucci-Guyon, E., Smola, H., Nodder, S., Babinet, C., Krieg, T., and Martin, P. 2000. Impaired wound healing in embryonic and adult mice lacking vimentin. J Cell Sci 113 (Pt 13):2455-2462). Rhamm is shown to be required for cell migration and its loss results in aberrant formation/resolution of granulation tissue.

Regulation of Rhamm expression affects growth of mesenchymal stem cells in skin. An abundance of Rhamm promotes a myofibroblastic lineage, while a loss of Rhamm promotes differentiation along an adipocyte lineage. Therefore, in one embodiment, Rhamm inhibitory reagents are used on skin cells to obtain a variety of mesenchymal stem cell populations.

Collectively, the present data indicate that Rhamm is a fibrogenic factor expressed predominantly in cells that do not necessarily form parenchymal units. Moreover, the present results indicate that ERK1,2 activity in Rh-/- granulation tissue fibroblasts is aberrant and contributes to the miscuing of granulation tissue formation/resolution of Rh-/- excisional wounds. Thus, these results indicate that Rhamm is a cellular factor required both for sustaining ERK1,2 activity in different subcellular compartments and for the appropriate temporal regulation of trafficking active ERK1,2 during wound repair. The loss of Rhamm expression results in an inherent migration defect related to a reduced ability of fibroblasts to orient towards haptotactic cues. Cell surface Rhamm [also designated CD168] is important in this migration since anti-Rhamm antibodies blocked the haptotaxis/invasion of Wt fibroblasts but not Rh-/- fibroblasts. Reduced migration is linked to defective mechanisms of disassembly of the actin cytoskeleton.

It is seen that active Mek1 can compensate for loss of Rhamm in performing these cell functions. Co-expression of $Rh^{FL}$ and Mek1 did not have an additive effect on these restored properties relative to $Rh^{FL}$ or Mek1 expressed alone indicating that Rhamm and activated Mek1 act on the same motogenic signaling pathway.

Identified herein is a physiological function of Rhamm as a fibrogenic factor required for appropriate timing and spatial regulation of granulation tissue formation and resolution. A major consequence of Rhamm loss on granulation tissue formation/resolution is reduced/delayed fibroplasia associated with sparse/heterogeneous fibroblast density, enhanced neutrophil accumulation and aberrant mesenchymal differentiation as indicated by reduced myofibroblast conversion, reduced myoblast fusion and increased subcutaneous adipocyte accumulation within wound tissue.

These data indicate that an underlying defect associated with these repair deficiencies in Rh-/- wounds is de-regulated ERK1,2 activation kinetics that impact upon signaling pathways promoting fibroblast migration. This conclusion is supported by the demonstration that Rh-/- fibroblasts retain their inability to appropriately activate ERK1,2 in culture and resulting migration defects, as measured by several locomotion assays. These defects are rescued by expression of mutant active Mek1, an ERK1,2 kinase activator.

We have previously reported that Rh-/- fibroblasts exhibit reduced proliferation in culture (Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). Oncogene 22:6873-6882). However, our current data do not provide support for an essential role of Rhamm in mitotic spindle formation or cell cycle regulation during wound repair in dermal fibroblasts in vivo, as judged by the lack of detectable differences in proliferation or apoptotic indices within Rh-/- vs. litter-matched Wt wound sites. Nevertheless, the slightly disorganized migration of Rhamm-/- fibroblasts in scratch wound assays on tissue culture plastic is consistent with a centrosomal defect that contributes to aberrant migration (Watanabe, T., Noritake, J., and Kaibuchi, K. 2005. Regulation of microtubules in cell migration. Trends Cell Biol 15:76-83). A role for Rhamm in collagen contraction has also been controversial.

Unexpectedly, however, our studies have revealed a role for Rhamm in recruitment/differentiation of myofibroblasts and contraction of the wound bed. As is increasingly reported and recognized (Bissell, M. J., Rizki, A., and Mian, I. S. 2003. Tissue architecture: the ultimate regulator of breast epithelial function. Curr Opin Cell Biol 15:753-762), both of these results emphasize the importance of context and the microenvironment in regulating cell signaling. Thus, data obtained in culture, especially on two-dimensional (2D) substrata are confirmed in vivo and in relevant microenvironments as described in the Examples.

Horizontal sections of Rhamm-/- wounds show fewer muscle fibers than in wildtype wounds (FIG. 10B). These results suggest a role for Rhamm in muscle differentiation consistent with its other known fibrogenic effects. Furthermore, CT scans of Rhamm-/- mice revealed that bone density is increased in mice lacking Rhamm compared to wildtype mice (FIG. 12). These results suggest that systemic depletion of Rhamm can result in bone loss and that conversely, administration of Rhamm agonists should increase bone density.

Lastly, the effects of Rhamm on muscle, adipocyte, myofibroblast and bone density indicate that this gene regulates msenchymal stem cell differentiation since bone marrow mesenchymal stem cells are responsible for replacing each of these mesenchymal cell lineages in large wounds.

Therefore, in one embodiment, it is provided the use of Rhamm as a fibrogenic factor required for appropriate cueing of migration and differentiation of mesenchymal stem cells which are necessary for various functions including wound repair, cartilage and bone formation, adipogenesis, muscle formation, and regulation of tissue injuries such as heart attacks and stroke injuries. Rhamm factor expression can be manipulated to increase or decrease the rate of fibrotic wound response, depending upon the desired response.

For example, in one embodiment, in burn victims or patients having large open surface wounds, the natural fibrotic wound response and contraction would result in amplified mesenchymal stem cell and macrophage recruitment and laying down of large tracks of collagen fibrils to cover the wound quickly for wound contraction. This often results in puckering of the skin and unsightly scarring. The manipulation of Rhamm expression by application of an anti-Rhamm agent may increase wound healing time by preventing wound contraction, but allow the wound to be filled in with adipocytes, without wound contraction or laying down of large collagen fibrils, and thus, result in scar-less healing of wounds. In one embodiment, the anti-Rhamm agent may be provided in an anti-burn cream or ointment that is applied to the wound. In another embodiment, the anti-Rhamm agent is combined with an antibiotic cream or ointment to prevent infection.

In another embodiment, the fibrotic wound response is desired to be increased, for example, in tissues wherein if there is large wound and due to unsafe conditions and the distance to travel to medical facilities is lengthy, it may desired to increase rates of wound repair. Thus, in one embodiment, Rhamm peptide mimetics or an HA-binding peptide is applied at such a dose to the wound to promote faster wound contraction. In another embodiment, the Rhamm peptide mimetic or HA-binding peptide is combined with an antibiotic cream or ointment to prevent infection.

VI. Agonist Rhamm Compound Agents

In one embodiment, the compounds capable of modulating, enhancing or increasing Rhamm expression and function include reagents that enhance Rhamm activity such as agonist antibodies and HA mimetics or expression of a Rhamm cDNA, which will promote various functions including, wound repair, wound contraction, muscle formation and differentiation, bone density, cartilage and bone formation, adipogenesis, and regulation of other tissue injuries.

In a preferred embodiment, a specific Rhamm agonist is used. For example, HA would be an agonist if it specifically interacted with Rhamm but although it binds to and activates Rhamm it also binds to many other proteins therefore it is a relatively non-specific agonist. Thus, in one embodiment, HA mimetics are much more specific to Rhamm and may be used as agonists of this particular function (e.g. HA binding) of Rhamm. While expression of Rhamm cDNA will enhance Rhamm function by increasing its protein production, agonist antibodies and HA mimetics will enhance Rhamm functions by activating the endogenous protein. For example, HA mimetics will bind to the HA binding sequence of Rhamm and mimic the ability of HA to promote Rhamm-mediated signaling.

A. Agonist Antibodies that Specifically Enhance Rhamm

The term "antibody" refers to a polypeptide encoded by an immunoglobulin gene or functional fragments thereof that specifically binds and recognizes an antigen (e.g., Rhamm)

The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)). Techniques for the production of single chain antibodies or recombinant antibodies (U.S. Pat. Nos. 4,946,778, 4,816, 567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545, 806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety (e.g., toxins). In one aspect the antibody modulates the activity of the protein.

The phrase "specifically binds to, or "selectively binds to" or "specifically immunoreactive with," or "selectively binds to" when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a Rhamm protein, polymorphic variants, alleles, orthologs, and conservatively modified variants, or splice variants, or portions thereof, can be selected to obtain only those polyclonal antibodies that are specifically immunoreactive with Rhamm proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

In some embodiments, the Rhamm modulator is an antibody (e.g., a polyclonal or monoclonal antibody) that specifically binds and/or inhibit Rhamm can be used using methods known in the art and may be used therapeutically as well. Such use of antibodies has been demonstrated by others and may be useful in the present invention to modulate Rhamm expression or function, such as by increasing or upregulating, or inhibiting or downregulating Rhamm. Rhamm antibodies can also be made to specific sequences that act as agonists, particularly when the antibody is used as an Fab fragment. An example would be preparation of antibodies to the HA binding sequence of Rhamm, then proteolysis of the antibody to an Fab fragment will enhance signaling in an HA-like manner (Hall et al., *Cell Commun Adhes.* 2002 September-December; 9(5-6):273-83, 2002). Rhamm specific antibodies can be made by a number of methods known in the art. In one embodiment, specific Rhamm antibodies are generated by first amplifying and cloning cDNA fragments of SEQ ID NOS: 1 or 3. A cDNA sequence such as SEQ ID NO: 1 is amplified and cloned, and then expressed peptide fragments of Rhamm from the cloned cDNAs are obtained.

In another embodiment, peptide fragments are synthesized to generate peptide fragments. These peptide fragments may include portions of the Rhamm 60 aa isoform insertion and may contain the adjacent Rhamm amino acid sequence.

Since synthesized peptides are not always immunogenic on their own, the peptides are conjugated to a carrier protein before use. Appropriate carrier proteins include, but are not limited to, Keyhole limpet hemacyanin (KLH), bovine serum albumin (BSA) and ovalbumin (OVA). The conjugated peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal antibodies can be purified by passing the harvested antibodies through an affinity column. However, monoclonal antibodies are preferred over polyclonal antibodies and can be generated according to standard methods known in the art of creating an immortal cell line which expresses the antibody.

Nonhuman antibodies are highly immunogenic in human thus limiting their therapeutic potential. In order to reduce their immunogenicity, nonhuman antibodies need to be humanized for therapeutic application. Through the years, many researchers have developed different strategies to humanize the nonhuman antibodies. One such example is using "HuMAb-Mouse" technology available from MEDAREX, Inc. (Princeton, N.J.). "HuMAb-Mouse" is a strain of transgenic mice that harbors the entire human immunoglobin (Ig) loci and thus can be used to produce fully human monoclonal Rhamm antibodies.

Immunoblotting using the specific antibodies of the invention with a control sequence should not produce a detectable signal at preferably 0.5-10 fold molar excess (relative to the Rhamm detection), more preferably at 50 fold molar excess and most preferably no signal is detected at even 100 fold molar excess.

Hall, C L, Wang F S and Turley E A, Src-/- fibroblasts are defective in their ability to disassemble focal adhesions in response to phorbol ester/hyaluronan treatment, *Cell Commun Adhes.* 2002 September-December; 9(5-6):273-83 describe the preparation of agonist antibodies, which may be useful in modulating Rhamm and upregulating Rhamm and its function. This modulation is used to increase wound repair and contraction, bone density and formation, and muscle formation and differentiation.

B. Rhamm cDNA Expression

Substantially identical nucleic acids encoding sequences of Rhamm inhibitors can be isolated using nucleic acid probes and oligonucleotides under stringent hybridization conditions, by screening libraries. Alternatively, expression libraries can be used to clone these sequences, by detecting expressed homologues immunologically with antisera or purified antibodies made against the core domain of nucleic acids encoding Rhamm inhibitor sequences as described above.

Gene expression of RHAMM can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

To obtain high level expression of a cloned gene or nucleic acid sequence, such as those cDNAs encoding nucleic acid sequences encoding Rhamm, Rhamm agonists, and Rhamm inhibitors such as an siRNA Rhamm inhibitor and related nucleic acid sequence homologues, one typically subclones a sequence (e.g., nucleic acid sequences encoding Rhamm and Rhamm agonists inhibitors such as a siRNA Rhamm inhibitor and related nucleic acid sequence homologue) into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding Rhamm inhibitors such as a siRNA Rhamm inhibitor or a subsequence thereof. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant RHAMM inhibitors peptides to provide convenient methods of isolation, e.g., His tags. In some case, enzymatic cleavage sequences (e.g., SEQ ID NO: 7 Met-(His)$_n$-Ile-Glu-Gly-Arg which form the Factor Xa cleavage site) are added to the recombinant Rhamm inhibitor peptides.

Bacterial expression systems for expressing the Rhamm inhibitor peptides and nucleic acids are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of a Rhamm inhibitor, which can then purified using standard techniques (see, e.g., Colley et al., *J. Biol. Chem.* 264:17619-17622 (1989); Guide to Protein Purification, in Methods in Enzymology, vol. 182 (Deutscher, ed., 1990)). Transformation of cells is performed according to standard techniques (see, e.g., Morrison, *J. Bact.* 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, lipofectamine, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing RHAMM inhibitor peptides and nucleic acids.

After the expression vector is introduced into the cells, the transfected cells are cultured under conditions favoring expression of Rhamm inhibitors such as a siRNA Rhamm inhibitor and related nucleic acid sequence homologues.

C. Peptides and Peptide Mimetics

One of the inventors describes the use of hyaluronan-binding peptides in treating disorders associated with altered tissue levels of hyaluronan or RHAMM, such as cancer, inflammation, and fibrotic disorders associated with tissue trauma (See Turley, U.S. Pat. No. 6,271,344). Furthermore these hyaluronan binding peptides also reduce bacterial infections in wounds (Zaleski K J, et al., 2006 *Antimicrob. Agents Chemother.* 50: 3856-60, and hereby incorporated by reference) and these antimicrobial effects are likely one of the mechanisms for the anti-fibrotic effects of these peptides.

In one embodiment, peptides and peptide mimetics can be made to block known Rhamm interactions, thereby inhibiting Rhamm function by competitively binding to Rhamm co-factors. In one embodiment, CD44 interactions with Rhamm are blocked. In another embodiment, the polypeptides are administered in a high enough dosage such that Rhamm recruitment occurs.

In other embodiments, polypeptides which mimic Rhamm co-factors and Rhamm mimetics, are used to increase Rhamm recruitment, expression and function. In one embodiment, such peptides can be made or designed based on Rhamm-binding protein sequences and functional portions of those sequences.

In another embodiment, a hyaluronan mimicking peptide is used to modulate Rhamm function. The sequence of a preferred hyaluronan mimicking peptide is substantially identical to the following peptides: YDSEYESE (SEQ ID NO: 8), YDSeYeSe (SEQ ID NO: 9) and YDSEYeSE (SEQ ID NO: 10), (GCU-NAG)$_n$(SEQ ID NO:11), and is similar to HA such that the HA-binding region of Rhamm will recognize the polypeptide and bind to it. The residuesSuch a peptide is expected increase Rhamm within the wound site and increase Rhamm:hyaluronan interactions are involved in regulating wound repair and contraction, muscle formation and bone density formation. Methods for designing, making and preparing HA mimetics are also described in Ziebell, MR and Prestwich GD, 2004, Interaction of Peptide Mimics of Hyaluronic Acid with the Receptor of Hyaluronan Mediated Motility (Rhamm), *J. of Computer Aided Molecular Design*, v 18, 597-614; and Ziebell M R, Zhao Z-G, Luo B, Luo Y, Turley E A, and Prestwich GD. 2001. Peptides that mimic glycosaminoglycans: high-affinit ligands for a hyaluronan binding domain. *Chemistry and Biology* v 8: 1081-1094], the teachings of both of which are hereby incorporated by reference in their entirety for all purposes.

The polypeptides can be chemically synthesized using methods well known in the art including, e.g., solid phase synthesis (see, e.g., Merrifield, *J. Am. Chem. Soc.,* 85:2149-2154 (1963) and Abelson et al., Methods in Enzymology, Volume 289: Solid-Phase Peptide Synthesis (1st ed. 1997)). Polypeptide synthesis can be performed using manual techniques or by automation. Automated synthesis can be achieved, for example, using Applied Biosystems 431A Peptide Synthesizer (Perkin Elmer). Alternatively, various fragments of the polypeptide can be chemically synthesized separately and then combined using chemical methods to produce the full length polypeptide. The sequence and mass of the polypeptides can be verified by GC mass spectroscopy.

In yet another embodiment, peptide mimetics of the polypeptides of the present invention are provided. A "peptide mimetic" or "peptidomimetic" includes any modified form of an amino acid chain, including, but not limited to, phosphorylation, capping, fatty acid modifications and including unnatural backbone and/or side chain structures. It will be readily apparent to those of skill in the art that a peptide mimetic comprises the structural continuum between an amino acid chain and a non-peptide small molecule. Peptide mimetics generally retain a recognizable polypeptide-like polymer unit structure. Thus, a peptide mimetic typically retains the function of binding to any target molecule that a natural polypeptide binds to. Other peptidomimetics and methods of making same will be known to those of skill in the art.

The polypeptides can be comprised of D- or L- amino acid residues. Once synthesized, the polypeptides can be modified, for example, by N-terminal acetyl- and C-terminal amide-groups. It is also contemplated that all polypeptides presently described can be made using modified amino acid residues. In certain embodiments, the peptides of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or mono-saccharide, and phosphates. Effects of such non-amino acid elements on the functionality of a polypeptide can be tested using the assay methods disclosed herein Synthesized polypeptides can be further isolated by HPLC to a purity of at least about 80%, preferably 90%, and more preferably 95%.

The polypeptides described herein can also be expressed recombinantly, especially when the polypeptide does not comprise "D" amino acid residues and contains modified residues such as "L-amino acid residues." This embodiment relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

Polymerase chain reaction or other in vitro amplification methods may also be useful, for example, to clone nucleic acid sequences that code for the polypeptides to be expressed, to make nucleic acids to use as probes for detecting the presence of encoding mRNA in physiological samples, for nucleic acid sequencing, or for other purposes. Nucleic acids amplified by the PCR reaction can be purified from agarose gels and cloned into an appropriate vector.

III. Blocking Rhamm Function Selectively Affects Subcutaneous vs. Visceral Fat Rhamm also displays an effect in modulation of adipose tissue development. Histology analysis of tissue sections through unwounded skin of Rhamm-/- mice showed that the subcutaneous layer of fat is 2-3 times thicker than in wild-type littermate skin and fibroblasts grown from Rhamm-/- wounds incorporated high levels of fat droplets detected by Bodipy uptake and reduced smooth muscle actin, detected by anti-smooth muscle actin antibodies. Furthermore, Rhamm-/- dermal fibroblasts converted to adipocytes when grown in adipogenic medium.

In contrast fibroblasts grown from litter matched wild-type wounds did not exhibit fat droplets, and expressed abundant smooth muscle actin. Rhamm-rescued dermal fibroblasts do not undergo adipogenic conversion when grown in adipogenic medium. Conversely, image analysis of Rhamm-/- mice showed that they have significantly less visceral fat and a lower bone density than wild-type litter mates. These data indicate that Rhamm has a differential effect on visceral vs. subcutaneous adipogenesis. Finally, it was also observed that the keratinocytes and hair follicles of Rhamm-/- wounds are abnormal.

Although it is well accepted that gene transcriptomes of visceral and subcutaneous fat differs (Vidal H, 2001 Ann Med 33: 547-55), to date the inventors are not aware of any other genes that have been individually identified to selectively affect subcutaneous vs. organ fat. Heretofore, there were no methods to differentially regulate visceral vs. subcutaneous adipogenesis; methods for regulating fibrogenesis were directed against genes that are ubiquitously expressed e.g. TGF-β with concomitant side effects.

The in vivo data herein showed that Rhamm is selective in its regulation of subcutaneous vs. visceral fat, and that this regulation is associated with effects on bone marrow stem cells since bone density is a measure of stem cell activity. These results indicate that Rhamm affects subcutaneous fat deposition through its ability to regulate mesenchymal stem cell differentiation, a conclusion substantiated by the effect of Rhamm loss on another mesenchymal stem cell type, myofibroblasts. Furthermore, hyaluronan/Rhamm interactions play a role in this effect on mesenchymal differentiation since HA binding peptides also promote adipogenesis. In addition to these in vivo effects, Rhamm-/- dermal fibroblasts spontaneously develop into adipocytes when cultures become crowded while wild type dermal fibroblasts do not.

The results further show that use of function-blocking Rhamm reagents provide signals that force differentiation into adipocytes. As well, Rhamm-/- dermal fibroblasts express very low levels of smooth muscle actin indicating that Rhamm also regulates development of this mesenchymal stem cell lineage.

With respect to mesenchymal and other skin stem cells, a unique advantage of using function-blocking Rhamm reagents for increasing subcutaneous fat is that its effects are selective: visceral fat, whose increased accumulation on body organs is associated with disease is decreased while subcutaneous fat is increased. This is an unusual effect and differentiates Rhamm's effects from other adipocyte promoting factors such as leptin that affects accumulation of both types of adipocytes. Thus, Rhamm reagents that block Rhamm function will not increase visceral fat, a direct result due to Rhamm's selective effect on adipocyte stem cells.

Another unique property of Rhamm is related to its very restricted expression in the adult human tissues. Rhamm is poorly or not expressed physiologically but is increased following tissue injury or transformation to the neoplastic state. Therefore, anti-Rhamm reagents such as blocking antibodies etc should have low toxicity. In fact, blocking Rhamm function could be beneficial to those with a tumor load or with inflammation-based diseases such arthritis since Rhamm has pro-oncogenic, pro-inflammatory functions.

Enhancing the formation of subcutaneous fat has further potential in plastic surgery since subcutaneous fat provides plumpness and firmness to skin. Aging skin contains less subcutaneous fat, therefore using the present methods, administering anti-Rhamm reagents to the desired area to promote subcutaneous fat formation results in plumper and more youthful appearing skin. The present method can replace current methods for transplanting adipocytes from other areas of the body (e.g., the thigh or buttocks), since this older procedure often exhibits a low success rate.

The present invention provides a method for selectively enhancing subcutaneous adipose tissue. The method comprises administering a compound that blocks Rhamm function to a subject, whereby adipocyte formation occurs in dermal fibroblasts and volume is added in a selected subcutaneous area in the subject. In some embodiments, the subject is a mammal, preferably a human.

In some embodiments, the Rhamm function that is blocked is Rhamm binding to CD44. In one embodiment, the compounds capable of blocking Rhamm function include antibodies, soluble recombinant Rhamm protein fragments, peptide mimetics, small chemical mimetics, siRNA, antisense oligos, and aptamers to promote adipocyte formation in wild type dermal fibroblasts in vitro as detected by positive Oil Red O staining. In another embodiment, the anti-Rhamm and Rhamm function blocking compounds are tested in vitro as detected by adiponectin staining.

Additionally, in some embodiments, compounds blocking hyaluronan function including hyaluronan fragments, peptide mimetics, small chemical mimetics may also be used to regulate adipogenesis and mesenchymal stem cell differentiation.

In another embodiment, function blocking Rhamm compounds are provided to smooth out skin that has been scarred by acne, cellulite, stretch marks, dark circles under the eye, or to augment and firm breast tissue. In addition to this application, function-blocking Rhamm compounds are used for reconstruction of tissues, including but not limited to breast (e.g. after surgery to remove tumors), face or limb (e.g. after car accident or burning). For such uses, Rhamm compounds are optionally used in conjunction with tissue grafting material or other procedures that enhance youthful skin or repair of damaged tissues.

In another embodiment, function blocking Rhamm compounds are administered for augmentation of subcutaneous fat to improve thermoregulation and/or improve immune function.

In yet another embodiment, function blocking Rhamm compounds are used to selectively inhibit visceral adipose tissue formation in a subject. In some embodiments, the subject is a mammal, preferably a human. Thus, a method for selectively inhibiting visceral adipose tissue formation in a subject is described, the method comprising: administering a compound that blocks Rhamm function to the subject, thereby selectively inhibiting visceral adipose tissue formation in the subject.

In another embodiment, the compounds capable of blocking Rhamm function include antibodies, soluble recombinant Rhamm protein fragments, peptide mimetics, small chemical mimetics, siRNA, antisense oligos, and aptamers to promote adipocyte formation in wild type dermal fibroblasts in vitro as detected by positive Oil Red O staining and/or by positive adiponectin.

In some embodiments, the subject is treated with the function blocking Rhamm compounds to prevent disease or to treat ongoing disease associated with increased organ fat including but not limited to cardiovascular disease, and other obesity associated diseases.

VII. Rhamm Function Blocking Agents

In one embodiment, the compounds capable of modulating, blocking or inhibiting Rhamm function include antibodies, soluble recombinant Rhamm protein fragments, peptide mimetics, small chemical mimetics, siRNA, antisense oligos, and aptamers to promote adipocyte formation in wild type dermal fibroblasts in vitro as detected by positive Oil Red O staining.

A. Antibodies that Specifically Block Rhamm

In some embodiments, the function blocking Rhamm compound is an antibody (e.g., a polyclonal or monoclonal antibody) that specifically binds and/or inhibits Rhamm. Antibodies can be used to modulate Rhamm using methods known in the art and such antibodies may be used therapeutically as well. Such use of antibodies has been demonstrated by others and may be useful in the present invention to inhibit or downregulate Rhamm. Rhamm specific antibodies can be made by a number of methods known in the art and as described in the sections above. The methods for identifying, making and humanizing antibodies are well known and described in the previous section.

In one embodiment, the antibody is used to inhibit or block Rhamm activity to decrease wound contraction. In another embodiment, the antibody is used to block or inhibit Rhamm activity to increase subcutaneous fat and adipogenesis and to reduce visceral fat in a particular region of the body. In another embodiment, the antibody is used to inhibit or block Rhamm activity to inhibit mesenchymal cell and fibroblast migration to prevent cell metastasis in cancer.

In one embodiment, specific Rhamm antibodies are generated by first amplifying and cloning cDNA fragments of SEQ ID NOS: 1 or 3. A cDNA sequence such as SEQ ID NO: 1 is amplified and cloned, and then expressed peptide fragments of Rhamm from the cloned cDNAs are obtained.

In another embodiment, peptide fragments are synthesized to generate peptide fragments. These peptide fragments may include portions of the Rhamm 60 aa isoform insertion and may contain the adjacent Rhamm amino acid sequence.

Since synthesized peptides are not always immunogenic on their own, the peptides are conjugated to a carrier protein before use. Appropriate carrier proteins include, but are not limited to, Keyhole limpet hemacyanin (KLH), bovine serum albumin (BSA) and ovalbumin (OVA). The conjugated peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal Rhamm antibodies can be purified by passing the harvested antibodies through an affinity column. However, monoclonal antibodies are preferred over polyclonal antibodies and can be generated according to standard methods known in the art of creating an immortal cell line which expresses the antibody.

Nonhuman antibodies are highly immunogenic in human thus limiting their therapeutic potential. In order to reduce their immunogenicity, nonhuman antibodies need to be humanized for therapeutic application. Through the years, many researchers have developed different strategies to humanize the nonhuman antibodies. One such example is using "HuMAb-Mouse" technology available from MEDAREX, Inc. (Princeton, N.J.). "HuMAb-Mouse" is a strain of transgenic mice that harbors the entire human immunoglobin (Ig) loci and thus can be used to produce fully human monoclonal Rhamm antibodies.

Immunoblotting using the specific antibodies of the invention with a control sequence should not produce a detectable signal at preferably 0.5-10 fold molar excess (relative to the Rhamm detection), more preferably at 50 fold molar excess and most preferably no signal is detected at even 100 fold molar excess.

B. Aptamers

In another embodiment, aptamer sequences which bind to specific RNA or DNA sequences can be made. Aptamers are synthetic oligonucleotides designed and selected to bind a certain target with high affinity and sensitivity, based upon unique folding and tertiary structure. Aptamers can be used as alternative candidates to antibodies in the present methods. As used herein, the terms "aptamer(s)"or "aptamer sequence(s)" are meant to refer to single stranded nucleic acids (RNA or DNA) whose distinct nucleotide sequence determines the folding of the molecule into a unique three dimensional structure. Aptamers comprising 15 to 120 nucleotides can be selected in vitro from a randomized pool of oligonucleotides ($10^{14}$-$10^{15}$ molecules). The "aptamers or aptamer sequences" comprise a degenerate sequence, and can further comprise fixed sequences flanking the degenerate sequence. The term "aptamer" as used herein further contemplates the use of both native and modified DNA and RNA bases, e.g. beta -D- Glucosyl-Hydroxymethyluracil.

Nucleic acids are easily synthesized or amplified by PCR; therefore a vast supply of consistent quality is available. Also, nucleic acids can easily be modified to incorporate tags, such as biotin or fluorescent molecules, for detection and/or immobilization. Additionally, aptamers are smaller (<25 kDa) and more stable than antibodies. Moreover, unlike the requirement of milligram quantities of protein or peptide for antibody production, only microgram quantities of protein or peptide are required for aptamer SELEX.

The idea of using single stranded nucleic acids (aptamers) as affinity molecules for proteins has shown modest progress. See Tuerk C, Gold L. (1990) Systematic evolution of ligands by exponential enrichment: RNA ligands to bacteriophage T4 DNA polymerase. *Science*. August 3;249(4968):505-10; Ellington A D, Szostak J W. (1990) In vitro selection of RNA molecules that bind specific ligands. *Nature*. August 30;346 (6287):818-22; and Ellington A D, Szostak J W. (1992) Selection in vitro of single-stranded DNA molecules that fold into specific ligand-binding structures. *Nature*. February 27;355 (6363):850-2. The concept is based on the ability of short oligomer (20-80 mer) sequences to fold, in the presence of a target, into unique 3-dimensional structures that bind the target with high affinity and specificity. Aptamers are generated by a process that combines combinatorial chemistry with in vitro evolution, commonly known as SELEX (Systematic Evolution of Ligands by Exponential Enrichment). Following the incubation of a protein with a library of DNA or RNA sequences (typically $10^{14}$ molecules in complexity) protein-DNA complexes are isolated, the DNA is amplified, and the process is repeated until the sample is enriched with sequences that display high affinity for the protein of interest. Since the selection pressure is high affinity for the target, aptamers with low nanomolar affinities may be obtained. Aptamers offer advantages over protein-based affinity reagents because nucleic acids possess increased stability, ease of regeneration (PCR or oligonucleotide synthesis), and simple modification for detection and immobilization.

Aptamer sequences can be isolated through methods such as those disclosed in co-pending U.S. patent application Ser. No. 10/934,856 (published as U.S. Patent Publication No. 20050142582), which is hereby incorporated by reference.

C. RNA Interference

In one embodiment, RNA interference is used to generate small double-stranded RNA (small interference RNA or siRNA) inhibitors to affect the expression of Rhamm generally through cleaving and destroying its cognate RNA. Small interference RNA (siRNA) is typically 19-22 nt double-stranded RNA. siRNA can be obtained by chemical synthesis or by DNA-vector based RNAi technology. Using DNA vector based siRNA technology, a small DNA insert (about 70 bp) encoding a short hairpin RNA targeting the gene of interest is cloned into a commercially available vector. The insert-containing vector can be transfected into the cell, and expressing the short hairpin RNA. The hairpin RNA is rapidly processed by the cellular machinery into 19-22 nt double stranded RNA (siRNA). In a preferred embodiment, the siRNA is inserted into a suitable RNAi vector because siRNA made synthetically tends to be less stable and not as effective in transfection.

siRNA can be made using methods and algorithms such as those described by Wang L, Mu FY. (2004) A Web-based Design Center for Vector-based siRNA and siRNA cassette. *Bioinformatics*. (In press); Khvorova A, Reynolds A, Jayasena S D. (2003) Functional siRNAs and miRNAs exhibit strand bias. *Cell*. 115(2):209-16; Harborth et al. (2003) *Antisense Nucleic Acid Drug Dev.* 13(2):83-105; Reynolds et al. (2004) *Nat Biotechnol.* 22(3):326-30 and Ui-Tei et al., (2004) *Nucleic Acids Res.* 32(3):936-48, which are hereby incorporated by reference.

Other tools for constructing siRNA sequences are web tools such as the siRNA Target Finder and Construct Builder available from GenScript, Oligo Design and Analysis Tools from Integrated DNA Technologies, or siDESIGN™ Center from Dharmacon, Inc. siRNA are suggested to be built using the ORF (open reading frame) as the target selecting region, preferably 50-100 nt downstream of the start codon. Because siRNAs function at the mRNA level, not at the protein level, to design an siRNA, the precise target mRNA nucleotide sequence may be required. Due to the degenerate nature of the genetic code and codon bias, it is difficult to accurately predict the correct nucleotide sequence from the peptide sequence. Additionally, since the function of siRNAs is to cleave mRNA sequences, it is important to use the mRNA nucleotide sequence and not the genomic sequence for siRNA design, although as noted in the Examples, the genomic sequence can be successfully used for siRNA design. However, designs using genomic information might inadvertently target introns and as a result the siRNA would not be functional for silencing the corresponding mRNA.

Rational siRNA design should also minimize off-target effects which often arise from partial complementarity of the sense or antisense strands to an unintended target. These effects are known to have a concentration dependence and one way to minimize off-target effects is often by reducing siRNA concentrations. Another way to minimize such off-target effects is to screen the siRNA for target specificity.

In one embodiment, the siRNA can be modified on the 5'-end of the sense strand to present compounds such as fluorescent dyes, chemical groups, or polar groups. Modification at the 5'-end of the antisense strand has been shown to interfere with siRNA silencing activity and therefore this position is not recommended for modification. Modifications at the other three termini have been shown to have minimal to no effect on silencing activity.

It is recommended that primers be designed to bracket one of the siRNA cleavage sites as this will help eliminate possible bias in the data (i.e., one of the primers should be upstream of the cleavage site, the other should be downstream of the cleavage site). Bias may be introduced into the experiment if the PCR amplifies either 5' or 3' of a cleavage site, in part because it is difficult to anticipate how long the cleaved mRNA product may persist prior to being degraded. If the amplified region contains the cleavage site, then no amplification can occur if the siRNA has performed its function.

Substantially identical nucleic acids encoding sequences of Rhamm inhibitors can be isolated using nucleic acid probes and oligonucleotides under stringent hybridization conditions, by screening libraries. Alternatively, expression libraries can be used to clone these sequences, by detecting expressed homologues immunologically with antisera or purified antibodies made against the core domain of nucleic acids encoding Rhamm inhibitor sequences.

Gene expression of RHAMM can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

To obtain high level expression of a cloned gene or nucleic acid sequence, such as those cDNAs encoding nucleic acid sequences encoding Rhamm, Rhamm inhibitors such as the siRNA Rhamm inhibitor and related nucleic acid sequence homologues, one typically subclones a sequence (e.g., nucleic acid sequences encoding Rhamm and Rhamm inhibitors such as a siRNA Rhamm inhibitor and related nucleic acid sequence homologue) into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding Rhamm inhibitors such as a siRNA Rhamm inhibitor or a subsequence thereof. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant RHAMM inhibitors peptides to provide convenient methods of isolation, e.g., His tags. In some case, enzymatic cleavage sequences (e.g., SEQ ID NO: 7 Met-(His)g-Ile-Glu-Gly-Arg which form the Factor Xa cleavage site) are added to the recombinant Rhamm inhibitor peptides. Bacterial expression systems for expressing the Rhamm inhibitor peptides and nucleic acids are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of a Rhamm inhibitor, which can then purified using standard techniques (see, e.g., Colley et al., *J. Biol. Chem.* 264:17619-17622 (1989); Guide to Protein Purification, in Methods in Enzymology, vol. 182 (Deutscher, ed., 1990)). Transformation of cells is performed according to standard techniques (see, e.g., Morrison, *J. Bact.* 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, lipofectamine, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing RHAMM inhibitor peptides and nucleic acids.

After the expression vector is introduced into the cells, the transfected cells are cultured under conditions favoring expression of Rhamm inhibitors such as a siRNA Rhamm inhibitor and related nucleic acid sequence homologues.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

In a preferred embodiment, SEQ ID NO: 1 is used to design siRNA targeting Rhamm using design methods and algorithms known in the art (see, e.g., Reynolds et al., *Nat Biotechnol.* 22(3):326-30 (2004). Factors used in designing the siRNA include, e.g., low G/C content, a bias towards low internal stability at the sense strand 3'-terminus, lack of inverted repeats, and sense strand base preferences (e.g., positions 3, 10, 13 and 19).

In another embodiment, web-based siRNA designing tools from Genescript may be used to design siRNA sequences that target Rhamm. Such tools typically provide the top candidate siRNA sequence and also perform BLAST screening (Altschul et al. (1990) "Basic local alignment search tool." *J. Mol. Biol.* 215:403-410) on each resulting siRNA sequence.

D. Antisense Oligonucleotides

In another embodiment, antisense oligonucleotides which inhibit Rhamm and other candidate genes can be designed. Antisense oligonucleotides are short single-stranded nucleic acids, which function by selectively hybridizing to their target mRNA, thereby blocking translation. Translation is inhibited by either RNase H nuclease activity at the DNA:RNA duplex, or by inhibiting ribosome progression, thereby inhibiting protein synthesis. This results in discontinued synthesis and subsequent loss of function of the protein for which the target mRNA encodes.

In a preferred embodiment, antisense oligos are phosphorothioated upon synthesis and purification, and are usually 18-22 bases in length. It is contemplated that the Rhamm and other candidate gene antisense oligos may have other modifications such as 2'-O-Methyl RNA, methylphosphonates, chimeric oligos, modified bases and many others modifications, including fluorescent oligos.

In a preferred embodiment, active antisense oligos should be compared against control oligos that have the same general chemistry, base composition, and length as the antisense oligo. These can include inverse sequences, scrambled sequences, and sense sequences. The inverse and scrambled are recommended because they have the same base composition, thus same molecular weight and Tm as the active antisense oligonucleotides. Rational antisense oligo design should consider, for example, that the antisense oligos do not anneal to an unintended mRNA or do not contain motifs known to invoke immunostimulatory responses such as four contiguous G residues, palindromes of 6 or more bases and CG motifs.

Antisense oligonucleotides can be used in vitro in most cell types with good results. However, some cell types require the use of transfection reagents to effect efficient transport into cellular interiors. It is recommended that optimization experiments be performed by using differing final oligonucleotide concentrations in the 1-5 µm range with in most cases the addition of transfection reagents. The window of opportunity, i.e., that concentration where you will obtain a reproducible antisense effect, may be quite narrow, where above that range you may experience confusing non-specific, non-antisense effects, and below that range you may not see any results at all. In a preferred embodiment, down regulation of the targeted mRNA (e.g., Rhamm mRNA SEQ ID NO: 1) will be demonstrated by use of techniques such as northern blot, real-time PCR, cDNA/oligo array or western blot. The same endpoints can be made for in vivo experiments, while also assessing behavioral endpoints.

For cell culture, antisense oligonucleotides should be re-suspended in sterile nuclease-free water (the use of DEPC-treated water is not recommended). Antisense oligonucleotides can be purified, lyophilized, and ready for use upon re-suspension. Upon suspension, antisense oligonucleotide stock solutions may be frozen at −20° C. and stable for several weeks.

E. Peptides and Peptide Mimetics

One of the inventors describes the use of hyaluronan-binding peptides in treating disorders associated with altered tissue levels of hyaluronan or RHAMM, such as cancer, inflammation, and fibrotic disorders associated with tissue trauma (See Turley, U.S. Pat. No. 6,271,344). Furthermore these hyaluronan binding peptides also reduce bacterial infections in wounds (Zaleski KJ, et al., 2006 Antimicrob. Agents Chemother. 50: 3856-60, and hereby incorporated by reference) and these antimicrobial effects are likely one of the mechanisms for the anti-fibrotic effects of these peptides.

In one embodiment, peptides and peptide mimetics can be made to block known Rhamm interactions, thereby inhibiting Rhamm function by competitively binding to Rhamm co-factors. In one embodiment, CD44 interactions with Rhamm are blocked. In another embodiment, the polypeptides are administered in a high enough dosage such that Rhamm recruitment occurs.

In other embodiments, polypeptides, such as an HA-binding peptide or Rhamm mimetics, are used to block Rhamm function. In one embodiment, such peptides can be made or designed based on Rhamm protein sequences, SEQ ID NO: 2 and 4, and functional portions of those sequences.

In another embodiment, a hyaluronan binding peptide is used to modulate Rhamm function. In a preferred embodiment, a peptide such as the peptides described by one of the inventors previously in Turley, U.S. Pat. No. 6,271,344, which is hereby incorporated by reference, is used. The sequence of a preferred hyaluronan binding peptide is substantially identical to SEQ ID NO: 5, STMMRSHKTRSH HV, and is similar to the HA binding region of Rhamm in that both have coiled coil secondary structure and similar spacing of key binding basic amino acids (BX7B "motifs"). The residues that are bolded and underlined above in SEQ ID NO:5 are responsible for Rhamm binding to HA The Rhamm HA binding domain sequence is KIKHVVKL K (SEQ ID NO: 6). The underlined and bolded residues show the residues in the peptide which bind to hyaluronan and mimic the Rhamm sequence. The phage peptide is expected to compete with Rhamm for hyaluronan within the wound site and is essentially a Rhamm peptide mimetic. As described in Example 7, the peptide will promote adipogenesis within the wound site indicating that Rhamm:hyaluronan interactions are involved in regulating adipogenesis.

The polypeptides can be chemically synthesized using methods well known in the art including, e.g., solid phase synthesis (see, e.g., Merrifield, *J. Am. Chem. Soc.,* 85:2149-2154 (1963) and Abelson et al., Methods in Enzymology, Volume 289: Solid-Phase Peptide Synthesis (1st ed. 1997)). Polypeptide synthesis can be performed using manual techniques or by automation. Automated synthesis can be achieved, for example, using Applied Biosystems 431A Peptide Synthesizer (Perkin Elmer). Alternatively, various fragments of the polypeptide can be chemically synthesized separately and then combined using chemical methods to produce the full length polypeptide. The sequence and mass of the polypeptides can be verified by GC mass spectroscopy.

In yet another embodiment, peptide mimetics of the polypeptides of the present invention are provided. A "peptide mimetic" or "peptidomimetic" includes any modified form of an amino acid chain, including, but not limited to, phosphorylation, capping, fatty acid modifications and including unnatural backbone and/or side chain structures. It will be readily apparent to those of skill in the art that a peptide mimetic comprises the structural continuum between an amino acid chain and a non-peptide small molecule. Peptide mimetics generally retain a recognizable polypeptide-like polymer unit structure. Thus, a peptide mimetic typically retains the function of binding to any target molecule that a natural polypeptide binds to. Other peptidomimetics and methods of making same will be known to those of skill in the art.

The polypeptides can be comprised of D- or L- amino acid residues. Once synthesized, the polypeptides can be modified, for example, by N-terminal acetyl- and C-terminal amide-groups. It is also contemplated that all polypeptides presently described can be made using modified amino acid residues. In certain embodiments, the peptides of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or mono-saccharide, and phosphates. Effects of such non-amino acid elements on the functionality of a polypeptide can be tested using the assay methods disclosed herein Synthesized polypeptides can be further isolated by HPLC to a purity of at least about 80%, preferably 90%, and more preferably 95%.

The polypeptides described herein can also be expressed recombinantly, especially when the polypeptide does not comprise a "D" amino acid residues. This embodiment relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

Polymerase chain reaction or other in vitro amplification methods may also be useful, for example, to clone nucleic acid sequences that code for the polypeptides to be expressed, to make nucleic acids to use as probes for detecting the presence of encoding mRNA in physiological samples, for nucleic acid sequencing, or for other purposes. Nucleic acids amplified by the PCR reaction can be purified from agarose gels and cloned into an appropriate vector.

VIII. Administration and Delivery

The anti-Rhamm agents of the invention can be administered directly to a mammalian subject using any route known in the art, including e.g., by injection (e.g., intravenous, intraperitoneal, subcutaneous, intramuscular, or intradermal), inhalation, transdermal application, rectal administration, or oral administration. In one embodiment, the anti-Rhamm agent is administered subcutaneously. In another embodiment, the anti-Rhamm agent is administered topically. In a preferred embodiment, an effective amount of the anti-Rhamm compounds are administered via non-systemic, local administration, such as by peripheral administration which includes peripheral intramuscular, intraglandular, and subcutaneous administration routes.

Administration of the Rhamm inhibitory agents (e.g., antibodies, peptides and nucleic acids) of the invention can be in any convenient manner, e.g., by injection, intratumoral injection, intravenous and arterial stents (including eluting stents), catheter, oral administration, inhalation, transdermal application, or rectal administration. In some cases, the peptides and nucleic acids are formulated with a pharmaceutically acceptable carrier prior to administration. Pharmaceutically acceptable carriers are determined in part by the particular composition being administered (e.g., nucleic acid or polypeptide), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

The dose administered to a patient, in the context of the present invention should be sufficient to effect a beneficial therapeutic response in the patient over time. The dose will be determined by the efficacy of the particular vector (e.g. peptide or nucleic acid) employed and the condition of the patient, as well as the body weight or surface area of the patient to be treated. The size of the dose also will be determined by the existence, nature, and extent of any adverse side-effects that accompany the administration of a particular peptide or nucleic acid in a particular patient.

The terms "effective amount" or "amount effective to" or "therapeutically effective amount" refers to an amount sufficient to induce a detectable therapeutic response in the subject. In determining the effective amount of the vector to be administered in the treatment or prophylaxis of diseases or disorder associated with the disease, the physician evaluates circulating plasma levels of the polypeptide or nucleic acid, polypeptide or nucleic acid toxicities, progression of the disease (e.g., ovarian cancer), and the production of antibodies that specifically bind to the peptide. Typically, the dose equivalent of a polypeptide is from about 0.1 to about 50 mg per kg, preferably from about 1 to about 25 mg per kg, most preferably from about 1 to about 20 mg per kg body weight. In general, the dose equivalent of a naked c acid is from about 1 µg to about 100 µg for a typical 70 kilogram patient, and doses of vectors which include a viral particle are calculated to yield an equivalent amount of therapeutic nucleic acid.

For administration, polypeptides and nucleic acids of the present invention can be administered at a rate determined by the LD-50 of the polypeptide or nucleic acid, and the side-effects of the polypeptide or nucleic acid at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

In still further embodiments, about 5 to about 2000 LD 50 units of the anti-Rhamm compound are administered to said subject. More specifically, about 5, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about.730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1010, about 1020, about 1030, about 1040, about 1050, about 1060, about 1070, about 1080, about 1090, about 1100, about 1110, about 1120, about 1130, about 1140, about 1150, about 1160, about 1170, about 1180, about 1190, about 1200, about 1210, about 1220, about 1230, about 1240, about 1250, about 1260, about 1270, about 1280, about 1290, about 1300, about 1310, about 1320, about 1330, about 1340, about 1350, about 1360, about 1370, about 1380, about 1390, about 1400, about 1410, about 1420, about 1430, about 1440, about 1450, about 1460, about 1470, about 1480, about 1490, about 1500, about 1510, about 1520, about 1530, about 1540, about 1550, about 1560, about 1570, about 1580, about 1590, about 1600, about 1610, about 1620, about 1630, about 1640, about 1650, about 1660, about 1670, about 1680, about 1690, about 1700, about 1710, about 1720, about 1730, about 1740, about 1750, about 1760, about 1770, about 1780, about 1790, about 1800, about 1810, about 1820, about 1830, about 1840, about 1850, about 1860, about 1870, about 1880, about 1890, about 1900, about 1910, about 1920, about 1930, about 1940, about 1950, about 1960, about 1970, about 1980, about 1990 or about 2000 LD 50 units of the anti-Rhamm compound are administered to said subject.

The pharmaceutical compositions of the invention may also comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17$^{th}$ ed., 1989).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In one embodiment, the anti-Rhamm agent prepared as in a cream or lotion. Typically such compositions are prepared with purified water, preservatives, emollient and emulsion stabilizers and humectants used in many cosmetic preparations including, but not limited to, propylene glycol, parabens, cetearyl alcohol, also known as cetostearyl alcohol, polysorbate 60 (polyoxyethylene sorbitan monostearate), cetyl alcohol, and glycerine.

In certain circumstances it will be desirable to deliver the pharmaceutical compositions comprising the anti-Rhamm inhibitor peptides and nucleic acids disclosed herein parenterally, intravenously, intramuscularly, or even intraperitoneally as described in U.S. Pat. Nos. 5,543,158; 5,641,515 and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In one embodiment, an effective therapeutic amount of the anti-Rhamm compound in freeze-dried or liquid formulation is drawn into a syringe at a fixed dosage, for example, per 0.1 cc. Other dose dilutions are possible. Subcutaneous injections are made in multiple locations through the selected region of the body.

Topical anesthetics such as 4% lidocaine cream or cetacaine spray may be used to reduce the discomfort of the procedure. Topical antibiotics may also be used to reduce the risk of infection.

Kits. The present invention further provides kits for use within any of the above methods. Such kits typically comprise two or more components necessary for performing a diagnostic assay. Components may include compounds, reagents, containers and/or equipment. For example, one container within a kit may contain anti-Rhamm compounds contained in freeze-dried or liquid formulation. One or more additional containers may enclose elements, such as reagents or buffers, to be used in the assay. Such kits may also, or alternatively, contain a detection reagent as described above that contains a reporter group suitable for direct or indirect detection of antibody binding.

Kits can also be supplied for therapeutic uses. Thus, the subject composition of the present invention may be provided, usually in a lyophilized form, in a container. The anti-Rhamm compounds described herein are included in the kits with instructions for use, and optionally with buffers, stabilizers, biocides, and inert proteins. Generally, these optional materials will be present at less than about 5% by weight, based on the amount of polypeptide or nucleic acid, and will usually be present in a total amount of at least about 0.001% by weight, based on the anti-Rhamm compound concentration. It may be desirable to include an inert extender or excipient to dilute the active ingredients, where the excipient may be present in from about 1 to 99% weight of the total composition. The kits may further comprise a second therapeutic agent, e.g., an antiinflammatory agent, antibacterial or antibiotic agent, a chemotherapeutic agent.

IX. EXAMPLES

Example 1

Materials and Methods

Reagent Preparation

Medical grade HA prepared from bacterial fermentation (gift of Skye Pharma, London UK) was free of detectable proteins, DNA or endotoxins (Filion, M. C., and Phillips, N. C. 2001. Pro-inflammatory activity of contaminating DNA in hyaluronic acid preparations. J Pharm Pharmacol 53:555-561). The average molecular weight range and polydispersity of HA was 276.7 kDa and 1.221 kDa, respectively.

HA oligosaccharides ($MW_{avg}$ 10 kDa) (gift of Dr. F. Winnik, University of Montreal, QC) were prepared by partial digestion with testicular hyaluronidase and purification by gel filtration. Human plasma fibronectin (BRL), Ki67 (pAb, DAKO), α-smooth muscle actin (pAb, Santa Cruz), tenascin (pAb, Chemicon) and vimentin (pAb, Santa Cruz) antibodies and Oregon Green phalloidin (Molecular Probes) were used according to the manufacturer's instructions.

Function blocking, affinity purified anti-Rhamm antibodies (Zymed) were confirmed to be specific by Western blot and immunofluorescence assays of Rh-/- fibroblasts. Anti-CD44 antibodies (mAb, KM114 and IM7, Pharmingen) were confirmed to be specific using western and immunofluorescence analyses of CD44-/- dermal fibroblasts. Phospho-ERK1,2 antibodies (pAb, Cell Signaling Technology) were used for immunohistochemistry and immunofluorescence and phospho-ERK1,2 (mAb, Sigma) and pan-ERK1 antibodies (pAb, Santa Cruz,) were used for Western blot analyses. Secondary antibodies were anti-rabbit Alexa 555 (Molecular Probes), Texas-Red or FITC labeled goat anti-mouse/goat anti-rabbit (Jackson laboratories), HRP-goat anti-mouse (Biorad), HRP-goat anti-rabbit (Pharmingen), HRP-rabbit anti-goat (Santa Cruz) and were used according to manufacturer's instructions.

ABC staining system (Santa Cruz) was used for immunohistochemistry and ApoTag peroxidase in situ apoptosis detection kit (Chemicon) was used for quantification of apoptosis. FACE ERK1/2 ELISA kit (Active Motif) was used according to manufacturer's instructions to quantify ERK1/2 activation in response to FCS in Rh-/-, $Rh^{FL}$-, Mek1- and Mek1/$Rh^{FL}$-rescued cell lines. Mounting medium for immunofluorescence contained DAPI (Vectashield) while Cytoseal 60 (Richard-Allan Scientific) was used for mounting of tissue sections.

The Mek1 inhibitors, PD98059 and U0126 (50 μM and 10 μM respectively, Biosciences), were used according to manufacturer's instructions. BODIPY 493/503 was purchased from Invitrogen and was used according to manufacturer's instructions.

Many of the materials and methods used in the present Examples have been described in Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348; Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). Oncogene 22:6873-6882; and Schmits, R., Filmus, J., Gerwin, N., Senaldi, G., Kiefer, F., Kundig, T., Wakeham, A., Shahinian, A., Catzavelos, C., Rak, J., et al. 1997. CD44 regulates hematopoietic progenitor distribution, granuloma formation, and tumorigenicity. Blood 90:2217-2233, the teachings of which are hereby incorporated by reference for all purposes.

Rh-/- Mice; Mouse Embryonic Fibroblasts and Dermal Fibroblasts

All animal experiments were performed in accordance with regulations of the animal use subcommittee at the University of Western Ontario, London, Ontario, Canada. The preparation of Rh-/- mice and mouse embryonic fibroblasts (MEF), as well as genotyping of mice and fibroblasts, have been described in Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). Oncogene 22:6873-6882, hereby incorporated by reference. CD44-/- mice have been described in Schmits, R., Filmus, J., Gerwin, N., Senaldi, G., Kiefer, F., Kundig, T., Wakeham, A., Shahinian, A., Catzavelos, C., Rak, J., et al. 1997. CD44 regulates hematopoietic progenitor distribution, granuloma formation, and tumorigenicity. Blood 90:2217-2233 and hereby incorporated by reference. Dermal fibroblasts were isolated from explanted skin from newborn mice. For the isolation of cells from granulation tissue, wound punches were cut into small pieces and cultured with the dermal side facing down in complete cell culture medium (10% FCS, DMEM, antibiotic-antimycotic).

RT-PCR Analysis of Rhamm and CD44 mRNA

Rhamm mRNA was amplified as previously described (Tolg, C., Poon, R., Fodde, R., Turley, E. A., and Alman, B. A. 2003. Genetic deletion of receptor for hyaluronan-mediated motility (Rhamm) attenuates the formation of aggressive fibromatosis (desmoid tumor). Oncogene 22:6873-6882) and PCR products were detected by Southern analysis using Rhamm exons 14-16 as a radioactive probe. CD44 mRNA was amplified as previously reported (Schmits, R., Filmus, J., Gerwin, N., Senaldi, G., Kiefer, F., Kundig, T., Wakeham, A., Shahinian, A., Catzavelos, C., Rak, J., et al. 1997. CD44 regulates hematopoietic progenitor distribution, granuloma formation, and tumorigenicity. Blood 90:2217-2233). Amplification of β-actin mRNA was used as a loading control (Tolg, et al, Oncogene 22:6873-6882).

Western Blots

Western analyses of CD44, phospho-ERK1,2 and total ERK1,2 proteins were performed as described (Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348; Tolg, et al, 2003 Oncogene 22:6873-6882 and Schmits et al., 1997 Blood 90:2217-2233). Densitometry was performed using Image Quant 5.1 software (Molecular Dynamics).

Cell Culture and Transfection

Cell culture medium and culture conditions were described previously in Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348; and Tolg, C., et al. 2003. Genetic deletion of receptor for hyaluronan-mediated motility (Rhamm) attenuates the formation of aggressive fibromatosis (desmoid tumor). Oncogene 22:6873-6882. PDGF-BB (25 ng/ml), HA (500 ng/ml-1 mg/ml) or FCS (10%) were added to 24 hrs serum-starved, 50% sub-confluent fibroblasts on fibronectin (25 µg/ml)-coated dishes (Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348; Hall, C. L., Lange, L. A., Prober, D. A., Zhang, S., and Turley, E. A. 1996. pp60(c-src) is required for cell locomotion regulated by the hyaluronanreceptor RHAMM. Oncogene 13:2213-2224). To obtain a response to HA, cells were pre-treated with 5 nM PMA (Sigma) (26). Immortalized Rh-/- cells were transfected with Rh$^{FL}$ murine Rhamm and/or mutant active Mek1 (gift of N. Ahn, U. Colorado, Boulder) in the presence of Lipofectamine Plus (Invitrogen) as described previously in Zhang, S., Chang, M. C., Zylka, D., Turley, S., Harrison, R., and Turley, E. A. 1998. The hyaluronan receptor RHAMM regulates extracellular-regulated kinase. J Biol Chem 273: 11342-11348;. All transfectants were selected in G418 (1-5 mg/ml for 2-3 weeks).

Excisional Wounds and Histology

Wt and Rh-/- mice (3-18 month old) or male Sprague-Dawley rats were anaesthetized by Halothane inhalation. Two full thickness wounds were placed on denuded back skin using a 4 mm metal punch. In the case of the rat experiments, 200 ul of a vitrogen solution (type 1 collagen solution that gels at 35-37C) containing no peptide, 2-200 µg hyaluronan binding peptide or scrambled peptide was used to cover the wounds. Animals were housed in individual cages for the experimental period. Wounds were harvested at varying times using a 8 mm metal punch from similar locations on the backs of mice of the same gender and age. Harvested wounds were fixed overnight in 4% paraformaldehyde and paraffin embedded as described in Tolg, C., et al. 2003. Genetic deletion of receptor for hyaluronan-mediated motility (Rhamm) attenuates the formation of aggressive fibromatosis (desmoid tumor). Oncogene 22:6873-6882;. Numbered serial sections were cut perpendicular to the wound edge starting at the wound center. The first and last sections were stained with Masson's trichrome and non-stained sections were used for immunohistochemistry. To ensure that serial sections were cut starting at the wound center, wound samples were cut in half through the wound center prior to embedding In total, five experimental series were performed. In each experiment, wounds were harvested at four different time points (1, 3, 7, and 14 days after wounding). For each time point, four age and gender matched mice were used (two Rh-/- and two Wt mice). In total, for each time point, ten Rh-/- and ten Wt mice were analyzed.

Immunohistochemistry of Tissue Sections and Immunofluorescence of Cultured Cells Tissue sections were stained for collagen (Masson's trichrome), α-smooth muscle actin, vimentin and tenascin following manufacturer's recommendations. Staining was quantified after counter-staining with Harris Hematoxylin (EM SCIENCE) and mounting in Cytoseal 60 (Tullberg-Reinert, H., and Jundt, G. 1999. In situ measurement of collagen synthesis by human bone cells with a sirius red-based colorimetric microassay: effects of transforming growth factor beta2 and ascorbic acid 2-phosphate. Histochem Cell Biol 112:271-276). Immunofluorescence of phospho-ERK1,2 was done as previously published (49). For the detection of droplets of neutral lipids, paraformaldehyde-fixed cells were stained with BODIPY 493/503 (25 µg/ml) (Gocze, P. M., and Freeman, D. A. 1994. Factors underlying the variability of lipid droplet fluorescence in MA-10 Leydig tumor cells. Cytometry 17:151-158). Actin stress fibers were detected with Oregon-green phalloidin.

In vitro Wound and Invasion Assays

Confluent cell monolayers on fibronectin coated dishes were serum starved overnight Scratch wounds (1 or 3 mm) were made using sized cell scrapers, then covered with medium containing 10% FCS or 25 ng/ml PDGF-BB for 24-48hrs. Monolayers were fixed (3% paraformaldehyde), washed, stained with methylene blue (0.1% in methanol) then photographed using a Nikon inverted Eclipse TE 300 microscope. Images were analyzed for cell number per unit area of wound gap using Simple PCI (Compix). For 3D assays, collagen (Vitrogen 100, Cohesion) or Matrigel (BD) gels were prepared according to manufacturers instructions. Plastic inserts were placed in the gel center. Fibroblasts were (5×10$^5$ cells/ml) added to the outer gel ECM solution. After 24-48 hrs, plastic inserts were removed and the cell free space was filled with collagen containing 25 ng/ml PDGF-BB, 100 µg/ml HA, and 25 ng/ml fibronectin. Gels were fixed and analyzed 72 hrs later for cell numbers/unit area.

Time-lapse Cinemicrography

For experiments assessing the motogenic effects of HA and PDGF-BB, cells were plated onto fibronectin-coated tissue culture flasks at 50% sub-confluence overnight then serum-starved for 24 hrs. PDGF-BB or HA were added prior to filming as described (Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348; Hall, C. L., Collis, L. A., Bo, A. J., Lange, L., McNicol, A., Gerrard, J. M., and Turley, E. A. 2001. Fibroblasts require protein kinase C activation to respond to hyaluronan with increased locomotion. Matrix Biol 20:183-192). For quantifying the effect of FCS, fibroblasts were plated at 50% sub-confluence overnight onto tissue culture dishes that had been pre-coated with serum proteins. FCS was added after a 24 hr period of serum-starvation and cells were filmed as above.

Image Acquisition, Image Enhancement and Image Analysis

Masson's trichrome and eosin/hematoxylin stained tissue sections as well as vimentin, tenascin and phospho-ERK1,2 stained tissue section images were taken with air objectives (4×, NA=0.16; 20× NA=0.7) using an Olympus AX70 Provis microscope equipped with a Cooke SensiCam color camera (CCD Imaging) and Image Pro Plus Version 4.5.1.2.9 software (Media Cybernetics, Inc.). For quantification of pERK1,2 staining, images were saved as tiff files and quantification of histology staining was done using Photoshop 6.0 (Adobe). The area of blue Hematoxylin staining, representing number of cells, was quantified by selecting and counting blue pixels (select, color range, blue, Image, Histogram). After deletion of the selected blue pixels, the area stained by the peroxidase substrate DAB was identified by selecting shadows (select, color range, shadows) and quantified by measuring the number of pixels (Image, Histogram). The area stained with tenascin was quantified using Simple PCI imaging software (Compix). Images in FIG. 2A are composites of images taken with a 4× objective. The colors were enhanced using Photoshop 6.0 (Adobe, adjust, auto levels).

Scratch wound images were taken with air objectives (4× Nikon objective, air, NA=0.1, equipped with Hoffman modulation Contrast optics) using a Nikon Eclipse TE300 microscope equipped with a Hamamatsu digital camera (Hamamatsu) and Simple PCI imaging software (Compix). Images of the wounds were acquired using a Conica/Minolta Dimage Z3 digital camera equipped with 12× optical zoom. The wound area was quantified using Simple PCI imaging software (Compix). Immunofluorescent images of actin fluorescence (10× Nikon objective, air, NA=0.25) were also acquired using the Nikon Eclipse TE300 microscope and quantified using Photoshop 6.0 as above. Confocal images were taken using a 63× oil objective (Zeiss, NA=1.4) with a Zeiss 510 LSM Meta Confocal microscope using LSM 5 imaging software (Zeiss). Fluorescence intensity of images was measured using LSM 5 imaging software (Zeiss).

ERK1 and 2 are closely related MAP kinase isoforms that can perform different physiological functions. For example, ERK2 is required for normal embryogenesis (Yao, Y., Li, W., Wu, J., Germann, U. A., Su, M. S., Kuida, K., and Boucher, D. M. 2003. Extracellular signal-regulated kinase 2 is necessary for mesoderm differentiation. Proc Natl Acad Sci USA 100: 12759-12764), whereas gene knock out studies (Bost, F., Aouadi, M., Caron, L., and Binetruy, B. 2005. The role of MAPKs in adipocyte differentiation and obesity. Biochimie 87:51-56) indicate that ERK1 plays more subtle and specific roles in adult physiology including adipogenesis. Normally, both ERK1,2 are activated by Mek1 or 2 and regulate signaling pathways that control cell motility, invasion and cytoskeleton remodeling during migration in culture.

Our results showed that motility and invasion defects of Rh-/- fibroblasts are associated with an inability to sustain and maximally activate both of these MAP kinases following growth factor stimulation. These results are consistent with our previous evidence that Rhamm is required for PDGF-BB stimulated ERK1,2 activity in mesenchymal stem cells and for promoting migration by regulating signaling through upstream activators of ERK1,2 including HA, Src, Ras and FAK (Turley, E. A., Noble, P. W., and Bourguignon, L. Y. 2002. Signaling properties of hyaluronan receptors. J Biol Chem 277:4589-4592; Hall, C. L., Lange, L. A., Prober, D. A., Zhang, S., and Turley, E. A. 1996. pp60(c-src) is required for cell locomotion regulated by the hyaluronanreceptor RHAMM. Oncogene 13:2213-2224; Hall, C. L., Yang, B., Yang, X., Zhang, S., Turley, M., Samuel, S., Lange, L. A., Wang, C., Curpen, G. D., Savani, R. C., et al. 1995. Overexpression of the hyaluronan receptor RHAMM is transforming and is also required for H-ras transformation. Cell 82:19-26).

Loss of Rhamm resulted in an abnormal temporal regulation of the subcellular localization of ERK1,2 in response to certain fibrogenic factors. We showed that appropriately sustained activation and compartmentalization of active ERK1,2 is required for generating highly motile cells and for repairing large wound gaps. ERK1,2 regulates motility by both transcriptional and post-transcriptional mechanisms (Huang, C., Jacobson, K., and Schaller, M. D. 2004. MAP kinases and cell migration. J Cell Sci 117:4619-4628). Initiation and early phases of migration during wound repair do not appear to require transcription (Providence, K. M., and Higgins, P. J. 2004. PAI-1 expression is required for epithelial cell migration in two distinct phases of in vitro wound repair. J Cell Physiol 200:297-308). It is indicated that Rhamm affects the ability of ERK1,2 to regulate transcription of motility- and invasion-related genes. This indication is also consistent with the ability of Rhamm to activate a downstream effector of ERK1,2 signaling, AP1, in fibroblasts (Cheung, W. F., Cruz, T. F., and Turley, E. A. 1999. Receptor for hyaluronan-mediated motility (RHAMM), a hyaladherin that regulates cell responses to growth factors. Biochem Soc Trans 27:135-142) and in collagen-induced arthritis (Nedvetzki, S., Gonen, E., Assayag, N., Reich, R., Williams, R. O., Thurmond, R. L., Huang, J. F., Neudecker, B. A., Wang, F. S., Turley, E. A., et al. 2004. RHAMM, a receptor for hyaluronan-mediated motility, compensates for CD44 in inflamed CD44-knockout mice: A different interpretation of redundancy. Proc Natl Acad Sci USA 101:18081-18086).

Example 2

Rhamm Expression is Required for Granulation Tissue Formation and Resolution in Skin Wounds Rhamm expression increases during repair of human skin excisional wound xenografts (Lovvorn, H. N., 3rd, Cass, D. L., Sylvester, K. G., Yang, E. Y., Crombleholme, T. M., Adzick, N. S., and Savani, R. C. 1998. Hyaluronan receptor expression increases in fetal excisional skin wounds and correlates with fibroplasia. J Pediatr Surg 33:1062-1069; discussion 1069-1070) and following scratch wounding of smooth muscle cell monolayers (Savani, R. C., Wang, C., Yang, B., Zhang, S., Kinsella, M. G., Wight, T. N., Stern, R., Nance, D. M., and Turley, E. A. 1995. Migration of bovine aortic smooth muscle cells after wounding injury. The role of hyaluronan and RHAMM. J Clin Invest 95:1158-1168). As set forth herein, RT-PCR analysis of wounds confirmed that Rhamm expression was low in uninjured skin (FIG. 1A) but increased one day after injury. Elevated expression was sustained until day 3 then dropped so that by day 7, Rhamm mRNA levels were only slightly higher than in uninjured skin. These results indicate that Rhamm is expressed during the early stages of excisional skin wound repair, which include wound contraction, re-epithelialization and granulation tissue formation. The consequences of Rhamm loss to the integrity of these early processes were therefore examined.

Figure 1:
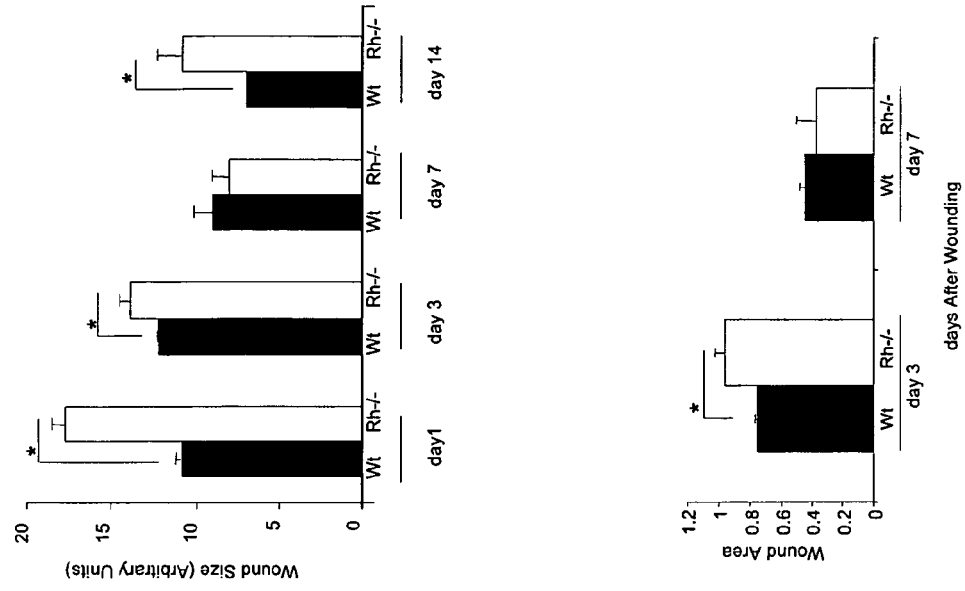
FIG. 1. Rhamm expression is regulated during early phases of wound repair and loss of Rhamm reduces wound contraction. A: Rhamm mRNA expression in excisional wounds: Rhamm mRNA expression is transiently up-regulated following excisional skin injury. The band (arrow) represents the full-length Rhamm PCR product. RT-PCR of β-actin mRNA was used as a loading control. B: Macroscopic quantification of wound contraction: Analyses of excisional areas of wounds show that Wt wounds contract more rapidly than Rh-/- wounds (day 3 p<0.05). The circled area denotes granulation tissue, which is reduced in Rh-/- vs. Wt wounds. Scale bars represent 3 mm. C: Microscopic quantification of wound contraction. Analyses of tissue sections reveal significant reductions in day 1-14 wound contraction (day 1 p<0.0001; day 3 p<0.05; day 14 p<0.001). Values represent the Mean and S.E.M. of 3 sections from 3 wounds of each genotype.
Figure 1:
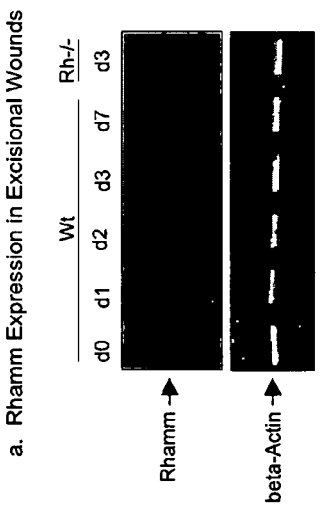
Figure 1:
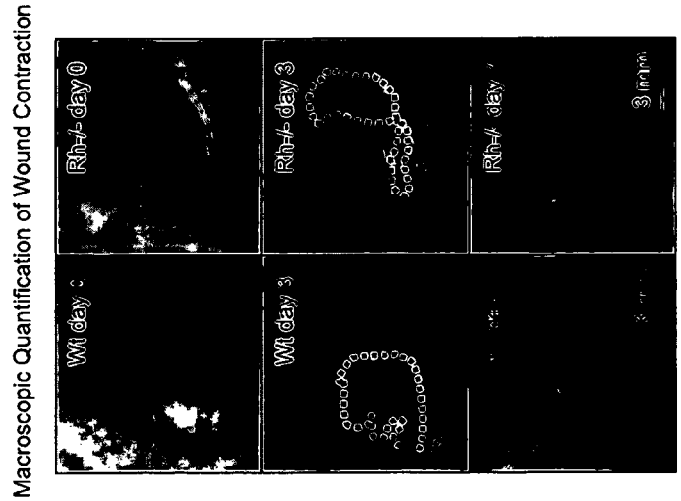

Contraction of day 3 Rh-/- wounds was significantly reduced compared to Wt wounds (FIG. 1B) but not at later times when wound areas were measured from photographs (FIG. 1B). However, when the distance between wound edges was measured using tissue sections cut through wound centers, significant reductions in the contraction of Rh-/- wounds could be detected between days 1-14 (FIG. 1C). Since granulation tissue myofibroblasts are significant contributors to wound contraction over this time frame, we next focused upon the consequences of Rhamm loss on granulation tissue formation/resolution.

A temporal spatial defect in the formation and resolution of granulation tissue was observed in Rh-/- vs. Wt wounds (FIGS. 2A, B and 3A). Tenascin-positive granulation tissue was abundant in day 3 Wt wounds, but decreased by day 7 and was largely resolved by day 14 (FIGS. 2A, B). In contrast, the area of tenascin-positive granulation tissue in day 3 and 7 Rh-/- wounds was significantly smaller than in Wt wounds. Day 14 wounds of Rh-/- mice were still strongly tenascin-positive, although the areas of these regions were highly variable between Rh-/- mice (FIGS. 2A, B). Interestingly, the pattern of tenascin staining in day 14 Rh-/- wounds was abnormal as the staining was "patchy", in contrast to day 14 Wt wounds (FIG. 2A). At day 21, Rh-/- wounds exhibited continued fibroplasia and aberrant differentiation of dermal structures such as hair follicles (FIG. 3A).

An additional difference in Rh-/- wounds was the transient appearance of a thick layer of subcutaneous adipocytes in day 1-3 Rh-/- wounds (FIGS. 2A, and 4A). Collectively, a prominent effect of Rhamm deficiency during wound repair is miscuing of signals required for the temporal regulation of granulation tissue formation and resolution necessary for appropriate dermal formation. This defect is consistent with the significantly thinner dermal layer of uninjured skin in Rh-/- vs. Wt mice (FIG. 3B).

Fibroplasia is a particularly prominent feature of granulation tissue in excisional skin wounds. The biological activities of fibroblasts and other mesenchymal cells, such as myofibroblasts, are key factors in the formation of early granulation tissue architecture (Reid, R. R., Said, H. K., Mogford, J. E., and Mustoe, T. A. 2004. The future of wound healing: pursuing surgical models in transgenic and knockout mice. J Am Coll Surg 199:578-585). Robust fibroplasia, as quantified by the density/unit area of granulation tissue fibroblasts, was apparent in day 3 Wt wounds and had increased by day 7 (FIG. 4A). Myofibroblasts, detected by smooth muscle actin staining, were also abundant in Wt wounds by day 7 (FIG. 4B).

In contrast, fibroplasia of day 3-7 Rh-/- granulation tissue was heterogeneous but blunted (FIG. 4A, circles) and there was a significant decrease in the number of myofibroblasts (FIG. 4B). Furthermore, Rh-/- granulation tissue was confirmed to contain abundant adipocytes, particularly at the wound edge, as indicated by the presence of vacuolated cells (FIG. 4A, arrows) which stained strongly with the lipophilic dye, BODIPY493/503 (17) (FIG. 10B). Rh-/- cells explanted from normal skin (day 0) and from day 7 wounds expressed less smooth muscle actin and accumulated more lipid than explanted Wt cells (FIG. 4C). Thus, deletion of Rhamm results in lower overall density and aberrant differentiation of granulation tissue fibroblasts.

A number of factors can affect fibroplasia as granulation tissue forms. An inflammatory response at the wound site is required to initiate fibroplasia, to provide growth factors and cytokines that attract fibroblasts into the wound site. These factors regulate fibroblast migration, survival and proliferation (O'Leary, R., Wood, E. J., and Guillou, P. J. 2002. Pathological scarring: strategic interventions. Eur J Surg 168:523-534). Rhamm regulates white cell trafficking in vivo and proliferation/apoptosis in culture (Adamia, S., Maxwell, C. A., and Pilarski, L. M. 2005. Hyaluronan and hyaluronan synthases: potential therapeutic targets in cancer. Curr Drug Targets Cardiovasc Haematol Disord 5:3-14; Turley, E. A., Noble, P. W., and Bourguignon, L. Y. 2002. Signaling properties of hyaluronan receptors. J Biol Chem 277:4589-4592).

Surprisingly, in vivo analysis revealed a significantly greater percentage of polymorphonuclear cells (cell/field) in Rh-/- day 3 and day 7 granulation tissue (65+6 and 40+12, respectively) compared to Wt (42+8 and 8+1, respectively); this suggested that Rhamm loss results in prolonged acute inflammation within excisional wounds. Neither cell proliferation (measured by the number of murine Ki-67-positive nuclei in granulation tissue) nor the rate of apoptosis (measured by ApopTag) were significantly different from Wt wounds. While these data do not rule out a role for fibroblast proliferation/apoptosis in the blunted fibroplasia observed in Rh-/- wounds, they suggest that these are not dominant factors.

Example 3

Rhamm Expression is Required to Sustain ERK1,2 Activation During Granulation Tissue Formation in Vivo and in Fibroblasts Responding to Growth Factors in Culture Fibroblast migration also contributes to fibroplasia and requires appropriate temporal regulation of signaling pathways such as ERK1,2, which provide cues for promoting and sustaining migration/invasion (Krueger, J. S., Keshamouni, V. G., Atanaskova, N., and Reddy, K. B. 2001. Temporal and quantitative regulation of mitogen-activated protein kinase (MAPK) modulates cell motility and invasion. Oncogene 20:4209-4218). Furthermore, these MAP kinases have been implicated in fibroblast differentiation into adipocytes, the most prominent being ERK1,2 (Bost, F., Aouadi, M., Caron, L., and Binetruy, B. 2005. The role of MAPKs in adipocyte differentiation and obesity. Biochimie 87:51-56).

Since we have shown that Rhamm associates with ERK1 in fibroblasts and that this association is required for PDGF-BB stimulated ERK1,2 activation (Zhang, S., Chang, M. C., Zylka, D., Turley, S., Harrison, R., and Turley, E. A. 1998. The hyaluronan receptor RHAMM regulates extracellular-regulated kinase. J Biol Chem 273:11342-11348), we hypothesized that the activity of these MAP kinases may be deficient in Rh-/- wound granulation tissue and contribute to aberrant fibroplasia (Hornberg, J. J., Binder, B., Bruggeman, F. J., Schoeberl, B., Heinrich, R., and Westerhoff, H. V. 2005. Control of MAPK signalling: from complexity to what really matters. Oncogene, 2005 August 25;24(36):5533-42). Both day 3 Wt and Rh-/- granulation tissue fibroblasts exhibited strong staining for the active forms of these kinases, as assessed with anti-phospho-ERK1,2 antibodies and standardized against total ERK1,2 protein (graph not shown). Staining intensity for phospho-ERK1,2 in Wt granulation tissue fibroblasts increased 6-fold by day 7 and did not drop significantly until day 13, whereas staining intensity of phospho-ERK1,2 prematurely decreased in Rh-/- granulation tissue by day 7 (data not shown). These changes in active ERK1,2 of Rh-/- vs. Wt granulation tissue fibroblasts were not due to decreases in total ERK1,2 protein levels since immunohistochemistry and immunoblot analyses revealed that Rh-/- fibroblasts expressed similar amounts of ERK1,2 protein compared to Wt fibroblasts in vivo.

These results indicate that ERK1,2 activity in Rh-/- granulation tissue fibroblasts is aberrant and contributes to the miscuing of granulation tissue formation/resolution of Rh-/- excisional wounds.

To determine whether the aberrant ERK1,2 activity observed in Rh-/- granulation tissue fibroblasts in vivo is a cell autonomous or micro-environmental defect, we quantified the response of isolated Rh-/- vs. $Rh^{FL}$ (full length Rhamm)-rescued Rh-/- fibroblasts to serum (FCS) (data not shown). ELISA analysis of active ERK1,2 revealed that both $Rh^{FL}$-rescued and Rh-/- fibroblasts activated ERK1,2 but activity declined more rapidly in Rh-/- fibroblasts. Western blot analysis revealed that both ERK1,2 were prematurely decreased in Rh-/- fibroblasts in response to serum when compared to $Rh^{FL}$-rescued or Wt fibroblasts. Confocal analysis showed that both $Rh^{FL}$-rescued and Rh-/- fibroblasts activate and target active ERK1,2 to the cell nucleus. However, activated ERK1,2 accumulated to a lesser extent and disappeared more rapidly from the nucleus of Rh-/- fibroblasts than the nucleus of the $Rh^{FL}$-rescued counterparts.

Importantly, very little activated ERK1,2 ever accumulated at the membrane of Rh-/- cell processes but were clearly activated and targeted to this compartment in Wt and $Rh^{FL}$-rescued fibroblasts. These results indicate that Rhamm is a cellular factor required both for sustaining ERK1,2 activity in different subcellular compartments and for the appropriate temporal regulation of trafficking active ERK1,2 during wound repair.

Example 4

Rhamm Expression is Required for Fibroblast Migration and Invasion in Culture Assays To assess whether or not Rh-/- fibroblasts have an inherent migration defect, their motogenic behavior was compared with $Rh^{FL}$-rescued fibroblasts using scratch wound and 3D collagen gel assays designed to mimic aspects of migration within the wound microenvironment (Reid, R. R., Said, H. K., Mogford, J. E., and Mustoe, T. A. 2004. The future of wound healing: pursuing surgical models in transgenic and knockout mice. J Am Coll Surg 199:578-585).

Significantly fewer Rh-/- than $Rh^{FL}$-rescued fibroblasts migrated across 3 mm scratch wounds in culture (FIG. 5A), as quantified both by the number of fibroblasts present in the wound gap and by time-lapse cinemicrography of wound edges. A similar difference was also noted between primary Rh-/- and litter-matched Wt fibroblasts (FIG. 13A). Vector analysis of time-lapse wound images revealed that Rh-/- fibroblasts were not restrained to a vertical orientation towards the wound gap, as was characteristic of the $Rh^{FL}$-rescued fibroblasts or Wt fibroblasts (FIG. 5A, FIG. 8A).

These results indicate that loss of Rhamm expression results in an inherent migration defect related to a reduced ability of fibroblasts to orient towards haptotactic cues.

The invasive properties of Rh-/- vs. Wt fibroblasts were also compared using 3D collagen type I gels. Gels were constructed with central plugs composed of collagen type I, PDGF-BB and HA, surrounded by fibroblasts enmeshed in collagen gel (FIG. 5B). Migration of primary Rh-/- dermal fibroblasts into the central collagen gel plug containing PDGF-BB and HA was reduced by almost 90% compared to that of litter-matched Wt fibroblasts (FIG. 5B) indicating an intrinsic and severe defect in haptotaxis and invasion of Rh-/- fibroblasts in vitro. A similar result was obtained with primary Rh-/- vs. Wt fibroblasts (FIG. 8B). Cell surface Rhamm [also designated CD168 (22)] is important in this migration since anti-Rhamm antibodies blocked the haptotaxis/invasion of Wt fibroblasts but not Rh-/- fibroblasts (FIG. 8B).

Efficient repair of excisional wounds also depends upon motility speed in response to motogens present in the microenvironment (See Ridley, A. J., Schwartz, M. A., Burridge, K., Firtel, R. A., Ginsberg, M. H., Borisy, G., Parsons, J. T., and Horwitz, A. R. 2003. Cell migration: integrating signals from front to back. Science 302:1704-1709). The velocity of migration stimulated by HA (FIG. 6A) or FCS (FIGS. 9A, 9B) was assessed directly using time-lapse cinemicrography of cells cultured on fibronectin-coated 2D tissue culture surfaces (Hall, C. L., Lange, L. A., Prober, D. A., Zhang, S., and Turley, E. A. 1996. pp60(c-src) is required for cell locomotion regulated by the hyaluronanreceptor RHAMM. Oncogene 13:2213-2224). Since both higher molecular weight HA (avg. 300 kDa) and HA oligosaccharides (avg. 10 kDa) promote cell motility (Turley, E. A., Noble, P. W., and Bourguignon, L. Y. 2002. Signaling properties of hyaluronan receptors. J Biol Chem 277:4589-4592), a mixture of these HA sizes was used for motility assays. Fibroblasts were pretreated with PMA to activate protein kinase C-dependent processes that permit motogenic responses to HA as described in Hall, C. L., Collis, L. A., Bo, A. J., Lange, L., McNicol, A., Gerrard, J. M., and Turley, E. A. 2001. Fibroblasts require protein kinase C activation to respond to hyaluronan with increased locomotion. Matrix Biol 20:183-192.

The HA mixture significantly promoted random motility of PMA-pretreated Wt fibroblasts (FIG. 6A), and stimulation was blocked by anti-Rhamm antibodies. The HA mixture did not enhance PMA-pretreated Rh-/- fibroblast random motility and anti-Rhamm antibodies had no effect (FIG. 6A). The inability of Rh-/- fibroblasts to increase random motility in response to HA was not due to lack of expression of CD44, which was expressed equally in both Rh-/- and Wt fibroblasts (FIG. 6B). A similar result was observed when Rh-/- and Wt fibroblasts were stimulated with serum (FIG. 9A). These results indicate that Rhamm expression is required for a motogenic response to HA and serum.

Cell migration and invasion require the rapid assembly/disassembly of the actin cytoskeleton. Since intracellular Rhamm forms associate with the actin cytoskeleton and are required for v-src-mediated actin cytoskeleton disassembly, we compared the ability of Rh-/- fibroblasts with $Rh^{FL}$-rescued fibroblasts to disassemble phalloidin-positive actin stress fibers in response to PDGF-BB. Unstimulated Rh-/- fibroblasts exhibited actin stress fibers similar to $Rh^{FL}$-rescued fibroblasts (data not shown). Immunofluorescent brightness of these structures, which provides a measure of disassembly, was also similar. However, following exposure to PDGF-BB, Rh-/- fibroblasts exhibited a significantly reduced ability to disassemble actin fibers compared to Wt fibroblasts (data not shown). These results indicate that reduced migration is linked to defective mechanisms of disassembly of the actin cytoskeleton.

Expression of Active Mek1 Rescues the Migration Defect of Rhamm-/- Fibroblasts.

Migratory behavior, including random motility, migration in scratch wound assays, invasion and cytoskeleton disassembly, have been shown previously to require ERK1,2 activity (27, 28). The Mek1 inhibitor, PD98059, was confirmed to significantly inhibit both motility and actin disassembly of Wt fibroblasts in response to PDGF-BB. However, this inhibitor had no effect on these parameters in Rh-/- fibroblasts (FIG. 9A).

Therefore, we asked whether the aberrant migratory properties of Rh-/- fibroblasts resulted directly from deficient ERK1,2 activity by expressing a mutant active Mek1 in Rhamm-deficient fibroblasts. Expression of mutant-active Mek1 restored the ability of Rh-/- fibroblasts to sustain activation of ERK1,2 in response to FCS. As well, active Mek1 expressing Rh-/- fibroblasts regained their ability to migrate across wound gaps and to invade collagen both at rates similar to $Rh^{FL}$-rescued fibroblasts (FIGS. 7A, B). Expression of mutant active Mek1 also restored the ability of Rh-/- fibroblasts to disassemble actin stress fibers and to increase random motility in response to PDGF-BB (FIG. 9B); collectively indicating that active Mek1 can compensate for loss of Rhamm in performing these cell functions.

Co-expression of Rh$^{FL}$ and Mek1 did not have an additive effect on these restored properties relative to Rh$^{FL}$ or Mek1 expressed alone (FIG. 7A, FIG. 9B) indicating that Rhamm and activated Mek1 act on the same motogenic signaling pathway.

Example 5

Administration of a Rhamm Blocking Agent to Facilitate Subcutaneous Adipose Tissue A subject is identified which has a need or which will benefit from space filling in a subcutaneous area(s). Examples of such subjects include, without limitation, persons with acne scars; scar tissue such as following burn or other surface trauma; persons who wish to add volume to an area such as breast or buttocks; persons with wrinkles or age-related skin changes; persons with diabetic skin ulcerations.

Reagents that block Rhamm function are provided. Such reagents include antisense nucleic acid molecules corresponding to the Rhamm coding sequence, siRNA directed to the Rhamm gene, anti-Rhamm antibodies, soluble recombinant Rhamm protein fragments and peptide mimetics. One or more of the function-blocking Rhamm reagents is provided to the subject. The route of administration is chosen, as appreciated by persons skilled in the art, based of the size of the area in which the subject wishes to have a result.

Accordingly, these blocking agents promote adipocyte formation in wild type dermal fibroblasts in vivo. This results in added volume in the subject's subcutaneous area. These results show that use of function-blocking Rhamm reagents provides signals that force differentiation into subcutaneous adipocytes. Thus, scars or wrinkles are filled in; tissue is volume is augmented.

Example 6

Administration of a Rhamm Blocking Agent to Facilitate Diminution of Visceral Adipose Tissue A subject is identified which has a need or which will benefit from a decrease or diminution of visceral adipose tissue. Examples of such subjects include, without limitation, persons with obesity, cardiovascular limitation or persons who wish to alter their appearance.

Reagents that block Rhamm function are provided. Such reagents include antisense nucleic acid molecules corresponding to the Rhamm coding sequence, siRNA directed to the Rhamm gene, anti-Rhamm antibodies, soluble recombinant Rhamm protein fragments and peptide mimetics. One or more of the function-blocking Rhamm reagents is provided to the subject. The route of administration is chosen, as appreciated by persons skilled in the art, based of the size of the area in which the subject wishes to have a result. For an affect on visceral fat, the administration route may be, e.g., systemic or intraperitoneal.

Accordingly, these blocking agents promote adipocyte formation in wild type dermal fibroblasts in vivo. This results in added volume in the subject's subcutaneous area. These results show that use of function-blocking Rhamm reagents provides signals that cause a diminution of the size and or quantity of visceral adipocytes. Thus, visceral fat is decreased.

Example 7

Bone Density and Visceral Fat Detection

The bone density of adult Rhamm-/- mice is significantly less than wild-type mice (FIG. 12). These results are consistent with our observations that loss of Rhamm modifies mesenchymal stem cell differentiation/trafficking since bone density can be used as a measure of mesenchymal stem cell differentiative capability in this case into bone.

In contrast to the consequence of Rhamm loss on subcutaneous adipogenesis, visceral fat was reduced in Rhamm-/- mice compared to wild-type littermates (FIG. 13). These results indicate that the Rhamm has a differential effect on subcutaneous vs. visceral fat, which derive from different mesenchymal stem cell lineages.

Hyaluronan binding peptides applied to rat excisional skin wounds increase subcutaneous adipogenesis at concentrations between 20-200 μg/wound site. Since these peptides resemble Rhamm in their hyaluronan binding characteristics and since these peptides also block Rhamm-dependent cell motility, it is likely the peptides are acting as Rhamm mimetics. These results suggest that interruption of hyaluronan/Rhamm interactions affects subcutaneous adipogenesis.

Example 8

Rhamm Modulation to Increase Bone Density and Muscle Differentiation

HA mimetics or Rhamm agonist antibodies or other reagents described in previous Examples are provided and then administered systemically or subcutaneously to a patient. A physician would determine an therapeutically effective dosage to be administered such that the administration of the reagent will increase bone density and muscle formation by activating the signaling functions of Rhamm. As another example, expressing or activating Rhamm in donor mesenchymal stem cells followed by their transplantation or injection IV would promote bone density or muscle mass.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:

1. A method of selectively enhancing subcutaneous adipose tissue formation in a mammal, said method comprising:
   administering a compound that reduces or inhibits Rhamm function to a mammal that is in need of or will benefit from selective enhancement of subcutaneous adipose tissue;
   where said administering comprises local administration to a subcutaneous area of said mammal, said subcutaneous area is an area in need of or that will benefit from local enhancement of subcutaneous adipose tissue, and said administering is in an amount sufficient to inhibit Rhamm function and induce adipocyte formation in said subcutaneous area, thereby enhancing subcutaneous adipose tissue formation in said area of said mammal.

2. The method of claim 1, wherein said method produces an increase in volume of said subcutaneous area.

3. The method of claim 1, wherein the selectively enhanced subcutaneous adipose tissue in a subject provides one or more results selected from the group consisting of smoothing out skin scarred by acne, smoothing out cellulite, smoothing out stretch marks, reducing dark circles under the eyes, reducing scar tissue formed from a burn or other surface trauma, increasing volume in buttocks, augmenting or firming breast tissue, and reducing wrinkles.

4. The method of claim 1, wherein the compound that reduces or inhibits Rhamm function is selected from the group consisting of an antibody that specifically binds Rhamm, a soluble recombinant Rhamm protein fragment, an aptamer, an antisense oligonucleotide, a Rhamm RNAi, a peptide, and a Rhamm peptide mimetic.

5. The method of claim 4, wherein said compound is a Rhamm peptide comprising the amino acid sequence of SEQ ID NO:5.

6. The method of claim 4, wherein said compound is a Rhamm peptide mimetic that is substantially homologous to SEQ ID No:5.

7. The method of claim 1, wherein said mammal is a human.

8. The method of claim 1, wherein the Rhamm function that is reduced is binding to CD44.

9. A method of selectively enhancing subcutaneous adipose tissue formation in an area of a mammal, said method comprising:
    selecting an area of said mammal that is in need of or that will benefit from enhancement of subcutaneous adipose tissue formation; and
    administering a compound that reduces or inhibits Rhamm function to said area, where said administering comprises local subcutaneous administration of said compound that reduces or inhibits Rhamm function to said area in an amount sufficient to inhibit Rhamm function and induce adipocyte formation in said subcutaneous area, thereby enhancing subcutaneous adipose tissue formation in said area of said mammal.

10. The method of claim 9, wherein said method produces an increase in volume of said subcutaneous area.

11. The method of claim 9, wherein said selected area is an area in need of or that will benefit from a result selected from the group consisting of smoothing out skin scarred by acne, smoothing out cellulite, smoothing out stretch marks, reducing dark circles under the eyes, reducing scar tissue formed from a burn or other surface trauma, increasing volume in buttocks, augmenting or firming breast tissue, and reducing wrinkles.

12. The method of claim 9, wherein the selectively enhanced subcutaneous adipose tissue development in a subject provides one or more results selected from the group consisting of smoothing out skin scarred by acne, smoothing out cellulite, smoothing out stretch marks, reducing dark circles under the eyes, reducing scar tissue formed from a burn or other surface trauma, increasing volume in buttocks, augmenting or firming breast tissue, and reducing wrinkles.

13. The method of claim 9, wherein said selecting comprises selecting an area in need of one or more results selected from the group consisting of smoothing out skin scarred by acne, smoothing out cellulite, smoothing out stretch marks, reducing dark circles under the eyes, reducing scar tissue formed from a burn or other surface trauma, increasing volume in buttocks, augmenting or firming breast tissue, and reducing wrinkles.

14. The method of claim 9, wherein the compound that reduces or inhibits Rhamm function is selected from the group consisting of an antibody that specifically binds Rhamm, a soluble recombinant Rhamm protein fragment, an aptamer, an antisense oligonucleotide, a Rhamm RNAi, a peptide, and a Rhamm peptide mimetic.

15. The method of claim 14, wherein said compound is a Rhamm peptide comprising the amino acid sequence of SEQ ID NO:5.

16. The method of claim 4, wherein said compound is a Rhamm peptide mimetic that is substantially homologous to SEQ ID No:5.

17. The method of claim 9, wherein said mammal is a human.

18. The method of claim 14, wherein the Rhamm function that is reduced is binding to CD44.

19. The method of claim 1, wherein said area in need of or that will benefit from local enhancement of subcutaneous adipose tissue is an area in need of or that will benefit from a result selected from the group consisting of smoothing out skin scarred by acne, smoothing out cellulite, smoothing out stretch marks, reducing dark circles under the eyes, reducing scar tissue formed from a burn or other surface trauma, increasing volume in buttocks, augmenting or firming breast tissue, and reducing wrinkles.

* * * * *

UNITED STATES PATENT AND TRADEMARK OFFICE
CERTIFICATE OF CORRECTION

| | | |
|---|---|---|
| PATENT NO. | : 8,715,653 B2 | Page 1 of 1 |
| APPLICATION NO. | : 12/515405 | |
| DATED | : May 6, 2014 | |
| INVENTOR(S) | : Turley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Twenty-eighth Day of July, 2015

Michelle K. Lee
*Director of the United States Patent and Trademark Office*